(12) United States Patent
Gupta et al.

(10) Patent No.: US 12,186,497 B2
(45) Date of Patent: Jan. 7, 2025

(54) INTRAVENOUS CANNULA

(71) Applicant: MedSource International LLC, Chaska, MN (US)

(72) Inventors: Neeraj Gupta, Gurgaon (IN); Calvin Todd Fagley, Excelsior, MN (US); Rachel Ann Sender, Eden Prairie, MN (US)

(73) Assignee: MedSource International LLC, Chaska, MN (US)

( * ) Notice: Subject to any disclaimer, the term of this patent is extended or adjusted under 35 U.S.C. 154(b) by 7 days.

(21) Appl. No.: 17/592,805

(22) Filed: Feb. 4, 2022

(65) Prior Publication Data

US 2023/0226312 A1 Jul. 20, 2023

(30) Foreign Application Priority Data

Jan. 14, 2022 (IN) .............................. 202211002361

(51) Int. Cl.
*A61M 25/00* (2006.01)
*A61M 25/06* (2006.01)

(52) U.S. Cl.
CPC .... *A61M 25/0097* (2013.01); *A61M 25/0075* (2013.01); *A61M 25/0606* (2013.01);
(Continued)

(58) Field of Classification Search
CPC .......... A61M 25/0097; A61M 25/0075; A61M 25/0631; A61M 25/0606; A61M 25/0618
See application file for complete search history.

(56) References Cited

U.S. PATENT DOCUMENTS 4,022,191 A 5/1977 Jamshidi
4,269,186 A 5/1981 Loveless et al.
(Continued)

FOREIGN PATENT DOCUMENTS

AU 2002340363 B2 8/2008
CA 2178267 A1 12/1996
(Continued)

OTHER PUBLICATIONS

"PTFE—Polytetrafluoroethylene", Summary of Properties, Jul. 4, 2017, Zeus Inc.
(Continued)

*Primary Examiner* — William R Carpenter
*Assistant Examiner* — Robert F Allen
(74) *Attorney, Agent, or Firm* — Dorsey & Whitney LLP

(57) ABSTRACT

Intravenous cannula devices configured to prevent blood backflow and needle prick injuries include a catheter assembly and a needle guard assembly. The catheter assembly includes a hub having a coaxial recess and a valve member positioned therein. The valve member is cylindrical and includes a distal surface having slits collectively defining prongs configured to open and close upon passage of a needle therethrough. Cannula devices configured to prevent needle stick injuries include a safety release component at a distal end of the needle guard assembly. The safety release component includes moveable locking elements configured to fit within an annular groove defined by a proximal portion of the hub upon movement of a needle through the safety release component. Proximal retraction of the needle through the safety release component causes the moveable locking elements to be displaced from the annular groove, thereby decoupling the catheter assembly from the needle guard assembly.

26 Claims, 20 Drawing Sheets

(52) U.S. Cl.
CPC .... *A61M 25/0631* (2013.01); *A61M 25/0693* (2013.01); *A61M 2025/0078* (2013.01); *A61M 2205/7536* (2013.01)

(56) References Cited

U.S. PATENT DOCUMENTS

| | | | |
|---|---|---|---|
| 4,747,831 A | 5/1988 | Kulli | |
| 4,762,516 A | 8/1988 | Luther et al. | |
| 4,778,453 A | 10/1988 | Lopez | |
| 4,832,696 A | 5/1989 | Luther et al. | |
| 4,834,718 A | 5/1989 | McDonald | |
| 4,846,805 A | 6/1989 | Sitar | |
| 4,878,902 A | 11/1989 | Wanderer | |
| 4,887,998 A | 12/1989 | Martin et al. | |
| 4,897,083 A | 1/1990 | Martell | |
| 4,917,668 A | 4/1990 | Haindl | |
| 4,929,241 A | 5/1990 | Kulli | |
| 4,932,940 A | 6/1990 | Walker et al. | |
| 4,944,725 A | 7/1990 | McDonald | |
| 4,944,728 A | 7/1990 | Carrell et al. | |
| 4,950,252 A | 8/1990 | Luther et al. | |
| 4,952,207 A | 8/1990 | Lemieux | |
| 4,964,854 A | 10/1990 | Luther | |
| 5,000,740 A | 3/1991 | Ducharme et al. | |
| 5,002,536 A | 3/1991 | Thompson et al. | |
| 5,013,304 A | 5/1991 | Russell et al. | |
| 5,030,205 A | 7/1991 | Holdaway et al. | |
| 5,078,694 A | 1/1992 | Wallace | |
| 5,092,845 A | 3/1992 | Chang | |
| 5,098,410 A | 3/1992 | Kerby et al. | |
| 5,108,379 A | 4/1992 | Dolgin et al. | |
| 5,120,319 A | 6/1992 | Van Heugten | |
| 5,135,504 A | 8/1992 | McLees | |
| 5,156,599 A | 10/1992 | Ranford et al. | |
| 5,195,974 A | 3/1993 | Hardy | |
| 5,195,992 A | 3/1993 | Dudar et al. | |
| 5,205,829 A | 4/1993 | Lituchy | |
| 5,215,525 A | 6/1993 | Sturman | |
| 5,215,528 A | 6/1993 | Purdy et al. | |
| RE34,416 E | 10/1993 | Lemieux | |
| 5,300,045 A | 4/1994 | Plassche | |
| 5,322,517 A | 6/1994 | Sircom et al. | |
| 5,328,482 A | 7/1994 | Sircom et al. | |
| 5,334,158 A | 8/1994 | McLees | |
| 5,344,408 A | 9/1994 | Partika | |
| 5,409,461 A | 4/1995 | Steinman | |
| 5,419,766 A | 5/1995 | Chang et al. | |
| 5,423,766 A | 6/1995 | Di | |
| 5,533,974 A | 7/1996 | Gaba | |
| 5,558,651 A | 9/1996 | Crawford et al. | |
| 5,562,631 A | 10/1996 | Bogart | |
| 5,599,310 A | 2/1997 | Bogert | |
| 5,601,532 A | 2/1997 | Gaba | |
| 5,601,535 A | 2/1997 | Byrne et al. | |
| 5,601,536 A | 2/1997 | Crawford et al. | |
| 5,611,781 A | 3/1997 | Sircom et al. | |
| 5,662,610 A * | 9/1997 | Sircom | A61M 5/3243 604/110 |
| 5,676,658 A * | 10/1997 | Erskine | A61M 5/3269 604/165.03 |
| 5,688,249 A | 11/1997 | Chang et al. | |
| 5,690,619 A | 11/1997 | Erskine | |
| 5,695,474 A | 12/1997 | Daugherty | |
| 5,697,907 A | 12/1997 | Gaba | |
| 5,702,367 A | 12/1997 | Cover et al. | |
| 5,713,876 A | 2/1998 | Bogert et al. | |
| 5,800,395 A | 9/1998 | Botich et al. | |
| 5,810,785 A | 9/1998 | Bogert et al. | |
| 5,830,189 A | 11/1998 | Chang | |
| 5,853,393 A | 12/1998 | Bogert | |
| 5,879,337 A | 3/1999 | Kuracina et al. | |
| 5,911,705 A | 6/1999 | Howell | |
| 6,004,294 A | 12/1999 | Brimhall et al. | |
| 6,050,976 A | 4/2000 | Thorne et al. | |
| 6,077,244 A | 6/2000 | Botich et al. | |
| 6,117,108 A | 9/2000 | Woehr et al. | |
| 6,203,527 B1 | 3/2001 | Zadini et al. | |
| 6,221,047 B1 | 4/2001 | Greene et al. | |
| 6,280,419 B1 | 8/2001 | Vojtasek | |
| 6,287,278 B1 | 9/2001 | Woehr et al. | |
| 6,287,317 B1 | 9/2001 | Makower et al. | |
| 6,379,337 B1 | 4/2002 | Mohammad M. B. B. S. | |
| 6,443,929 B1 | 9/2002 | Kuracina et al. | |
| 6,461,362 B1 | 10/2002 | Halseth et al. | |
| 6,491,707 B2 | 12/2002 | Makower et al. | |
| 6,533,759 B1 | 3/2003 | Watson et al. | |
| 6,582,402 B1 | 6/2003 | Erskine | |
| 6,595,954 B1 | 7/2003 | Luther et al. | |
| 6,595,955 B2 | 7/2003 | Ferguson et al. | |
| 6,616,630 B1 | 9/2003 | Woehr et al. | |
| 6,620,136 B1 | 9/2003 | Pressly et al. | |
| 6,623,458 B2 | 9/2003 | Woehr et al. | |
| 6,629,957 B1 | 10/2003 | Wiklund | |
| 6,629,959 B2 | 10/2003 | Kuracina et al. | |
| 6,652,490 B2 | 11/2003 | Howell | |
| 6,689,102 B2 | 2/2004 | Greene | |
| D491,266 S | 6/2004 | Cindrich et al. | |
| 6,749,588 B1 | 6/2004 | Cindrich et al. | |
| 6,796,962 B2 | 9/2004 | Ferguson et al. | |
| 6,860,871 B2 | 3/2005 | Kuracina et al. | |
| 6,872,193 B2 | 3/2005 | Shaw et al. | |
| 6,893,423 B2 | 5/2005 | Denolly | |
| 6,902,546 B2 | 6/2005 | Ferguson | |
| 6,942,652 B1 | 9/2005 | Pressly et al. | |
| 6,972,002 B2 | 12/2005 | Thorne | |
| 6,979,333 B2 | 12/2005 | Hammerslag | |
| 6,981,965 B2 | 1/2006 | Luther et al. | |
| 6,995,814 B2 | 2/2006 | Kanatsu | |
| 7,014,622 B1 | 3/2006 | Pressly et al. | |
| 7,037,292 B2 | 5/2006 | Carlyon et al. | |
| 7,179,244 B2 | 2/2007 | Smith et al. | |
| 7,186,239 B2 | 3/2007 | Woehr | |
| 7,255,685 B2 | 8/2007 | Pressly, Sr. et al. | |
| 7,264,613 B2 | 9/2007 | Woehr et al. | |
| 7,303,547 B2 | 12/2007 | Pressly et al. | |
| 7,341,573 B2 | 3/2008 | Ferguson et al. | |
| 7,344,516 B2 | 3/2008 | Erskine | |
| 7,347,853 B2 | 3/2008 | Difiore et al. | |
| 7,413,562 B2 | 8/2008 | Ferguson et al. | |
| 7,500,965 B2 | 3/2009 | Menzi et al. | |
| D592,302 S | 5/2009 | Stokes et al. | |
| 7,534,227 B2 | 5/2009 | Kulli | |
| 7,604,616 B2 | 10/2009 | Thoresen et al. | |
| 7,611,499 B2 | 11/2009 | Woehr et al. | |
| 7,625,360 B2 | 12/2009 | Woehr et al. | |
| 7,632,243 B2 | 12/2009 | Bialecki et al. | |
| 7,658,725 B2 | 2/2010 | Bialecki et al. | |
| 7,678,080 B2 | 3/2010 | Shue et al. | |
| 7,699,807 B2 | 4/2010 | Faust et al. | |
| 7,736,342 B2 | 6/2010 | Abriles et al. | |
| 7,753,877 B2 | 7/2010 | Bialecki et al. | |
| 7,753,887 B2 | 7/2010 | Botich et al. | |
| 7,785,296 B2 | 8/2010 | Muskatello et al. | |
| 7,828,774 B2 | 11/2010 | Harding et al. | |
| 7,951,121 B2 | 5/2011 | Weaver et al. | |
| 7,963,948 B2 | 6/2011 | Melsheimer | |
| 7,972,313 B2 | 7/2011 | Woehr et al. | |
| 8,062,252 B2 | 11/2011 | Alheidt et al. | |
| 8,070,725 B2 | 12/2011 | Christensen | |
| 8,105,288 B2 | 1/2012 | Keyser et al. | |
| 8,133,206 B2 | 3/2012 | Greene et al. | |
| 8,172,805 B2 | 5/2012 | Mogensen et al. | |
| 8,211,070 B2 | 7/2012 | Woehr et al. | |
| 8,235,946 B2 | 8/2012 | Molgaard-Nielsen | |
| 8,251,950 B2 | 8/2012 | Albert et al. | |
| 8,257,322 B2 | 9/2012 | Koehler et al. | |
| 8,282,605 B2 | 10/2012 | Tan et al. | |
| 8,308,685 B2 | 11/2012 | Botich et al. | |
| 8,308,691 B2 | 11/2012 | Woehr et al. | |
| 8,328,762 B2 | 12/2012 | Woehr et al. | |
| 8,333,735 B2 | 12/2012 | Woehr et al. | |
| 8,337,463 B2 | 12/2012 | Woehr et al. | |
| 8,377,040 B2 | 2/2013 | Burkholz et al. | |
| 8,382,721 B2 | 2/2013 | Woehr et al. | |

(56) References Cited

U.S. PATENT DOCUMENTS

| | | |
|---|---|---|
| 8,398,597 B2 | 3/2013 | Brimhall |
| 8,403,886 B2 | 3/2013 | Bialecki et al. |
| 8,454,574 B2 | 6/2013 | Weaver et al. |
| 8,454,579 B2 | 6/2013 | Fangrow |
| 8,460,247 B2 | 6/2013 | Woehr et al. |
| 8,540,728 B2 | 9/2013 | Woehr et al. |
| 8,568,372 B2 | 10/2013 | Woehr et al. |
| 8,585,660 B2 | 11/2013 | Murphy |
| 8,591,469 B2 | 11/2013 | Keyser et al. |
| 8,597,249 B2 | 12/2013 | Woehr et al. |
| 8,603,009 B2 | 12/2013 | Tan et al. |
| 8,647,301 B2 | 2/2014 | Bialecki et al. |
| 8,647,313 B2 | 2/2014 | Woehr et al. |
| 8,771,230 B2 | 7/2014 | White et al. |
| 8,784,386 B2 | 7/2014 | Baid |
| 8,795,198 B2 | 8/2014 | Tan et al. |
| 8,814,833 B2 | 8/2014 | Farrell et al. |
| D713,522 S | 9/2014 | Woehr et al. |
| D713,957 S | 9/2014 | Woehr et al. |
| 8,827,965 B2 | 9/2014 | Woehr et al. |
| 8,834,422 B2 | 9/2014 | Walker et al. |
| 8,845,584 B2 | 9/2014 | Ferguson et al. |
| 8,882,742 B2 | 11/2014 | Dikeman et al. |
| 8,936,575 B2 | 1/2015 | Moulton |
| 9,033,927 B2 | 5/2015 | Maan et al. |
| 9,095,683 B2 | 8/2015 | Hall et al. |
| 9,149,626 B2 | 10/2015 | Woehr et al. |
| 9,174,036 B2 | 11/2015 | Okamura et al. |
| 9,180,277 B2 * | 11/2015 | Erskine ............ A61M 25/0618 |
| 9,186,455 B2 | 11/2015 | Moyer |
| 9,278,195 B2 | 3/2016 | Erskine |
| 9,289,237 B2 | 3/2016 | Woehr et al. |
| 9,314,608 B2 | 4/2016 | Weaver et al. |
| 9,320,870 B2 | 4/2016 | Woehr |
| 9,370,641 B2 | 6/2016 | Woehr et al. |
| 9,402,964 B2 | 8/2016 | Crawford |
| 9,427,549 B2 | 8/2016 | Woehr et al. |
| 9,504,786 B2 | 11/2016 | Carlyon et al. |
| 9,555,220 B2 | 1/2017 | Koehler et al. |
| 9,555,221 B2 | 1/2017 | Koehler et al. |
| 9,604,035 B2 | 3/2017 | Keyser et al. |
| 9,623,210 B2 | 4/2017 | Woehr |
| 9,764,085 B2 | 9/2017 | Teoh |
| 9,775,972 B2 | 10/2017 | Christensen et al. |
| 9,775,973 B2 | 10/2017 | Keyser et al. |
| 9,782,546 B2 | 10/2017 | Woehr |
| 9,827,398 B2 | 11/2017 | White et al. |
| 9,844,646 B2 | 12/2017 | Knutsson |
| 9,844,648 B2 | 12/2017 | Nakajima et al. |
| 9,933,079 B2 | 4/2018 | Weaver et al. |
| 9,962,525 B2 | 5/2018 | Woehr |
| 10,028,691 B2 | 7/2018 | Goral et al. |
| 10,052,474 B2 | 8/2018 | Keyser et al. |
| 10,080,869 B2 | 9/2018 | Woehr et al. |
| 10,307,571 B2 | 6/2019 | Burkholz |
| 10,314,984 B2 | 6/2019 | Koehler et al. |
| 10,406,327 B2 | 9/2019 | Holm et al. |
| 10,449,331 B2 | 10/2019 | Lim et al. |
| 10,456,572 B2 | 10/2019 | Woehr |
| 10,500,375 B2 | 12/2019 | Isaacson et al. |
| 10,500,376 B2 | 12/2019 | Isaacson et al. |
| 10,548,522 B2 | 2/2020 | Akcay et al. |
| 10,589,081 B2 | 3/2020 | Servin De La Mora Godinez et al. |
| 10,596,351 B2 | 3/2020 | Liska |
| 10,625,067 B2 | 4/2020 | Al-Ali |
| 10,661,058 B2 | 5/2020 | Woehr |
| 10,675,440 B2 | 6/2020 | Abitabilo et al. |
| 10,682,499 B2 | 6/2020 | Isaacson et al. |
| 10,695,551 B2 | 6/2020 | Shevgoor et al. |
| 10,835,729 B2 | 11/2020 | Agrawal et al. |
| 10,850,068 B2 | 12/2020 | Teoh |
| 11,071,849 B2 | 7/2021 | Ng et al. |
| 2002/0161386 A1 | 10/2002 | Halseth et al. |
| 2002/0165497 A1 * | 11/2002 | Greene ............ A61M 25/0606 604/198 |
| 2002/0169418 A1 | 11/2002 | Menzi et al. |
| 2003/0060760 A1 | 3/2003 | Botich et al. |
| 2003/0083620 A1 | 5/2003 | Luther et al. |
| 2003/0100868 A1 | 5/2003 | Ferguson et al. |
| 2003/0199827 A1 | 10/2003 | Thorne |
| 2004/0049155 A1 | 3/2004 | Schramm |
| 2004/0059296 A1 | 3/2004 | Godfrey |
| 2004/0078003 A1 | 4/2004 | Smith et al. |
| 2004/0127854 A1 | 7/2004 | Leinsing et al. |
| 2004/0158208 A1 | 8/2004 | Hiejima |
| 2004/0168690 A1 | 9/2004 | Payne |
| 2004/0186434 A1 | 9/2004 | Harding et al. |
| 2004/0204681 A1 | 10/2004 | Thoresen et al. |
| 2004/0236288 A1 | 11/2004 | Howell et al. |
| 2004/0267204 A1 | 12/2004 | Brustowicz |
| 2005/0038384 A1 | 2/2005 | Li |
| 2005/0096592 A1 | 5/2005 | Carlyon et al. |
| 2005/0113755 A1 | 5/2005 | Greene et al. |
| 2005/0277879 A1 | 12/2005 | Daga |
| 2006/0036219 A1 | 2/2006 | Alvin |
| 2006/0041231 A1 | 2/2006 | Pressly et al. |
| 2006/0229556 A1 | 10/2006 | Pressly et al. |
| 2007/0191776 A1 * | 8/2007 | Bialecki ............ A61M 25/0631 604/164.08 |
| 2008/0097330 A1 | 4/2008 | King et al. |
| 2008/0119795 A1 * | 5/2008 | Erskine ............ A61M 25/0618 604/263 |
| 2008/0228150 A1 | 9/2008 | Jones et al. |
| 2009/0137958 A1 * | 5/2009 | Erskine ............ A61M 25/0625 604/164.08 |
| 2009/0209912 A1 | 8/2009 | Keyser et al. |
| 2009/0222003 A1 | 9/2009 | Otley |
| 2009/0312711 A1 | 12/2009 | Brimhall |
| 2010/0042048 A1 | 2/2010 | Christensen |
| 2010/0241087 A1 | 9/2010 | Moulton |
| 2011/0015573 A1 | 1/2011 | Maan et al. |
| 2011/0301551 A1 | 12/2011 | Koehler et al. |
| 2011/0306933 A1 | 12/2011 | Djordejevic et al. |
| 2011/0319825 A1 | 12/2011 | Goral et al. |
| 2012/0035552 A1 | 2/2012 | Woehr |
| 2012/0089101 A1 | 4/2012 | Carlyon et al. |
| 2012/0150118 A1 | 6/2012 | Keyser et al. |
| 2013/0030391 A1 | 1/2013 | Baid |
| 2013/0165868 A1 | 6/2013 | Isaacson et al. |
| 2013/0237928 A1 | 9/2013 | Fisher et al. |
| 2014/0025009 A1 * | 1/2014 | Erskine ............ A61M 25/0618 604/164.08 |
| 2014/0052022 A1 | 2/2014 | Tan et al. |
| 2014/0058357 A1 | 2/2014 | Keyser et al. |
| 2014/0200549 A1 | 7/2014 | Norkunas |
| 2014/0236099 A1 | 8/2014 | Nakagami et al. |
| 2014/0336582 A1 | 11/2014 | Tisci |
| 2014/0365809 A1 | 12/2014 | Higeta et al. |
| 2014/0371715 A1 | 12/2014 | Farrell et al. |
| 2015/0094751 A1 | 4/2015 | Chen et al. |
| 2015/0224267 A1 | 8/2015 | Farrell et al. |
| 2015/0265827 A1 | 9/2015 | Keyser et al. |
| 2015/0328438 A1 | 11/2015 | Baid |
| 2016/0008581 A1 | 1/2016 | Ang et al. |
| 2016/0175563 A1 | 6/2016 | Woehr et al. |
| 2016/0175576 A1 | 6/2016 | Neff et al. |
| 2016/0220161 A1 | 8/2016 | Goral et al. |
| 2016/0220791 A1 | 8/2016 | Akcay et al. |
| 2016/0271370 A1 | 9/2016 | Keyser et al. |
| 2016/0331935 A1 | 11/2016 | Saatchi et al. |
| 2016/0361490 A1 | 12/2016 | Phang et al. |
| 2016/0361519 A1 | 12/2016 | Teoh et al. |
| 2016/0374685 A1 | 12/2016 | Abbott et al. |
| 2017/0035992 A1 | 2/2017 | Harding et al. |
| 2017/0035995 A1 | 2/2017 | Shevgoor et al. |
| 2017/0043134 A1 | 2/2017 | Harding et al. |
| 2017/0120011 A1 | 5/2017 | Burkholz et al. |
| 2017/0120017 A1 | 5/2017 | Burkholz et al. |
| 2017/0274183 A1 | 9/2017 | Burkholz et al. |
| 2017/0319822 A1 | 11/2017 | Ang |
| 2017/0333642 A1 | 11/2017 | Shevgoor et al. |
| 2017/0361070 A1 | 12/2017 | Hivert |

(56) References Cited

U.S. PATENT DOCUMENTS

| | | |
|---|---|---|
| 2018/0064912 A1 | 3/2018 | Keyser et al. |
| 2018/0078741 A1 | 3/2018 | Stokes |
| 2018/0154119 A1 | 6/2018 | White et al. |
| 2018/0214673 A1 | 8/2018 | Ng et al. |
| 2018/0214682 A1 | 8/2018 | Woehr et al. |
| 2018/0256885 A1 | 9/2018 | Shevgoor et al. |
| 2018/0289932 A1 | 10/2018 | Isaacson et al. |
| 2018/0296149 A1 | 10/2018 | Goral et al. |
| 2018/0304048 A1 | 10/2018 | Knutsson |
| 2018/0311475 A1 | 11/2018 | Baid |
| 2018/0361119 A1 | 12/2018 | Goral et al. |
| 2019/0160264 A1 | 5/2019 | Isaacson |
| 2019/0262549 A1 | 8/2019 | Koehler et al. |
| 2019/0351210 A1 | 11/2019 | Solomon et al. |
| 2020/0094026 A1 | 3/2020 | Isaacson et al. |
| 2020/0094037 A1 | 3/2020 | Tran et al. |
| 2020/0121896 A1 | 4/2020 | Baid |
| 2020/0146605 A1 | 5/2020 | Paliwoda |
| 2020/0188634 A1 | 6/2020 | Woehr et al. |
| 2020/0197667 A1 | 6/2020 | Gupta |
| 2020/0261702 A1 | 8/2020 | Jewell et al. |
| 2021/0187249 A1* | 6/2021 | Lagana' ............ A61M 25/0618 |
| 2021/0308427 A1 | 10/2021 | Ng et al. |
| 2021/0370020 A1* | 12/2021 | Gupta .................. A61M 5/158 |
| 2021/0402143 A1 | 12/2021 | Yokota et al. |
| 2022/0249810 A1 | 8/2022 | Gupta |
| 2022/0355072 A1 | 11/2022 | Gupta et al. |

FOREIGN PATENT DOCUMENTS

| | | | |
|---|---|---|---|
| CA | 2033361 C | 11/2002 | |
| CA | 2710969 A1 | 7/2009 | |
| CN | 106659438 A | 5/2017 | |
| CN | 107427633 A | 12/2017 | |
| DE | 4442352 C1 | 12/1995 | |
| EP | 0747083 A2 | 12/1996 | |
| EP | 0747085 A2 | 12/1996 | |
| EP | 0750916 A2 | 1/1997 | |
| EP | 3209363 B1 | 3/2019 | |
| EP | 3622992 A1 | 3/2020 | |
| EP | 3622999 A1 | 3/2020 | |
| IN | 201911036272 A * | 1/2020 | ........ A61M 25/0028 |
| JP | 07024071 A | 1/1995 | |
| JP | 2001046507 A | 2/2001 | |
| JP | 2001190683 A | 7/2001 | |
| JP | 20041544364 A | 6/2004 | |
| JP | 2022551563 A | 12/2022 | |
| WO | 9308865 A1 | 5/1993 | |
| WO | 9413341 A1 | 6/1994 | |
| WO | 0168174 A2 | 9/2001 | |
| WO | 2007061718 A2 | 5/2007 | |
| WO | 2007098355 A1 | 8/2007 | |
| WO | 2010107645 A1 | 9/2010 | |
| WO | 2011152916 A1 | 12/2011 | |
| WO | 2013051242 A1 | 4/2013 | |
| WO | 2015161294 A1 | 10/2015 | |
| WO | 2016033143 A1 | 3/2016 | |
| WO | 2016063287 A1 | 4/2016 | |
| WO | 2016135293 A2 | 9/2016 | |
| WO | 2017042825 A2 | 3/2017 | |
| WO | 2018096549 A1 | 5/2018 | |
| WO | 2018217781 A1 | 11/2018 | |
| WO | 2019008432 A1 | 1/2019 | |
| WO | 2019152630 A1 | 8/2019 | |
| WO | 2020011663 A1 | 1/2020 | |
| WO | 2020120404 A1 | 6/2020 | |
| WO | 2020189466 A1 | 9/2020 | |
| WO | 2021048867 A1 | 3/2021 | |

OTHER PUBLICATIONS

International Search Report and Written Opinion dated Jul. 20, 2022 in connection with International Patent Application No. PCT/US2022/027597, 9 pages.

International Search Report and Written Opinion for PCT Application No. PCT/IN2018/050178, Dated Jun. 12, 2018, 8 pages.

International Search Report and Written Opinion dated Apr. 19, 2022 in connection with International Patent Application No. PCT/US2022/016002, 7 pages.

International Search Report and Written Opinion issued in International Application No. PCT/US2023/060554, mailed on May 9, 2023, 11 pages.

International Search Report and Written Opinion issued in International Application No. PCT/US2023/060560, mailed on Jun. 2, 2023, 10 pages.

Murty, "Use of Stainless Steels in Medical Applications", Medical Device Materials: Proceedings of the Material & Processes for Medical Devices Conference, pp. 288, 2003.

International Preliminary Report on Patentability issued in International Application No. PCT/US2022/016002, mailed on Aug. 24, 2023, 6 pages.

First Examination Report issued in Indian Patent Application No. 201911036272, mailed on Feb. 10, 2020, 5 pages.

Hearing Notice issued in Indian Patent Application No. 201911036272, mailed on Jul. 16, 2020, 2 pages.

International Preliminary Report on Patentability issued in International Application No. PCT/US2023/060554, mailed on Jul. 25, 2024, 10 pages.

International Preliminary Report on Patentability issued in International Patent Application No. PCT/US2023/060560, mailed on Jul. 25, 2024, 9 pages.

* cited by examiner

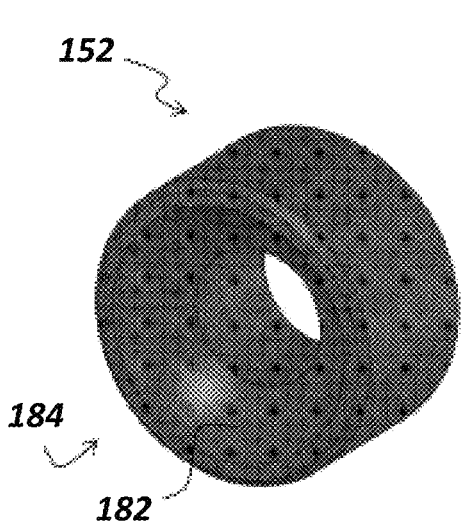 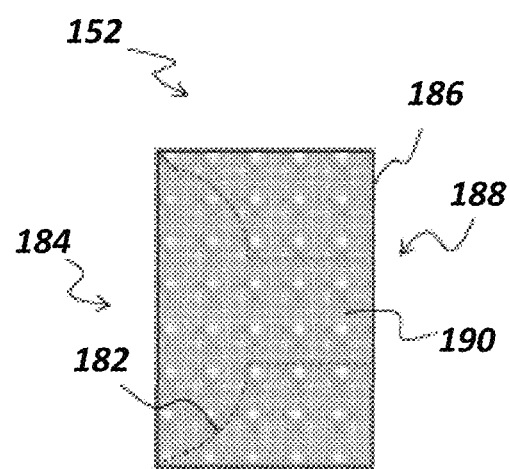
FIG. 7A  FIG. 7B
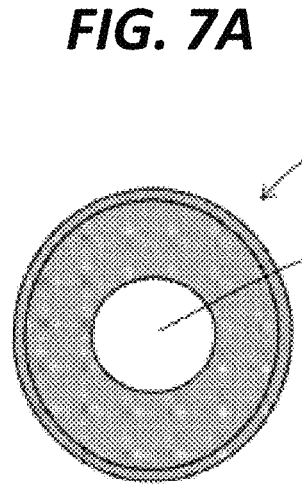 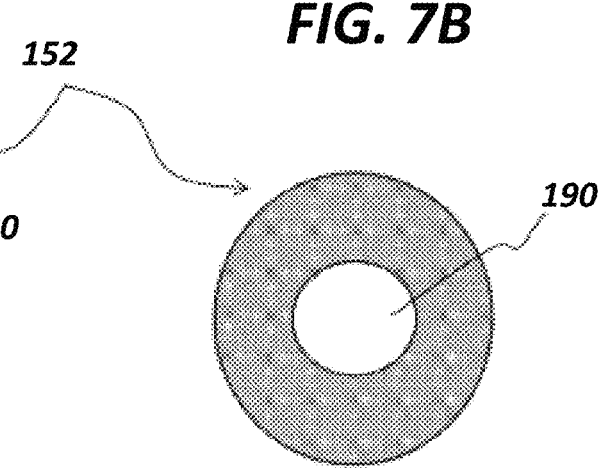
FIG. 7C  FIG. 7D

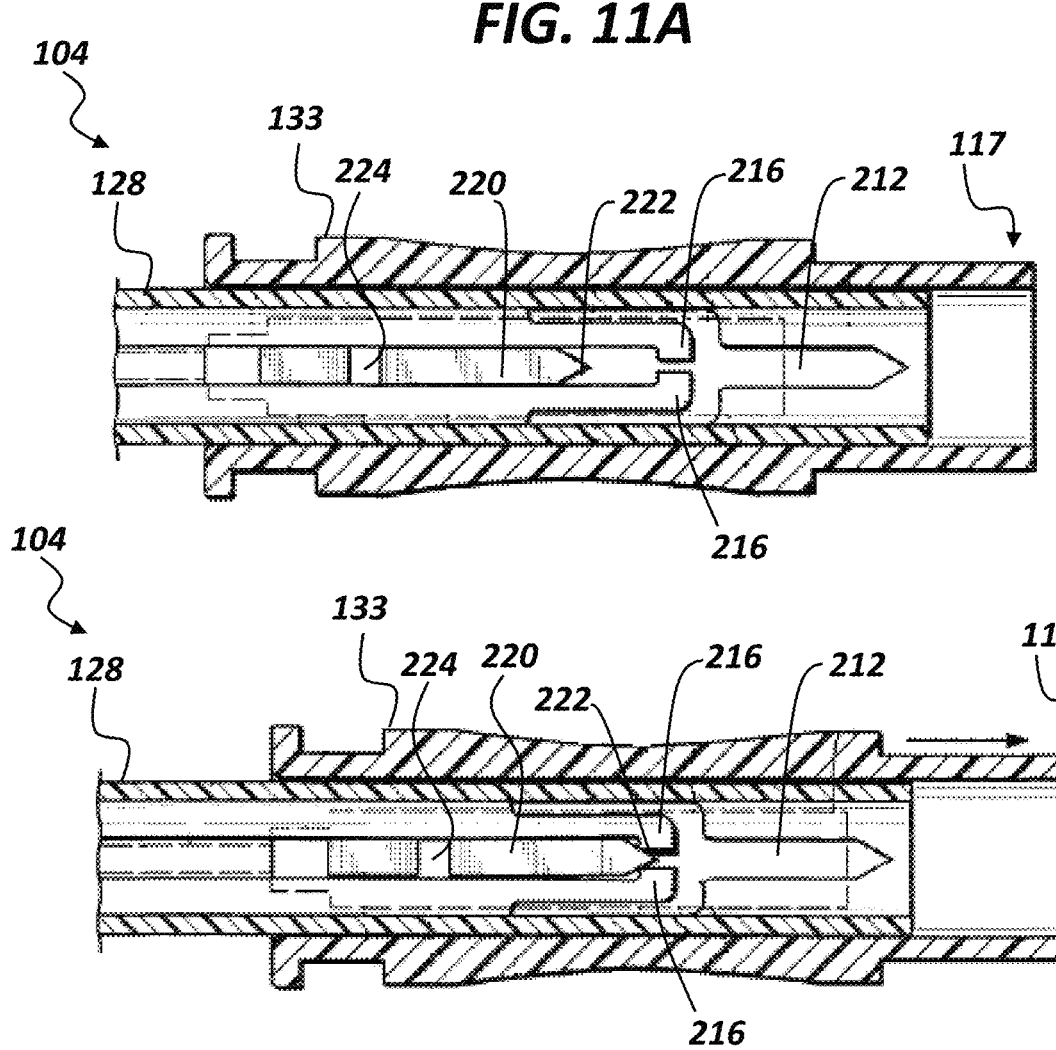

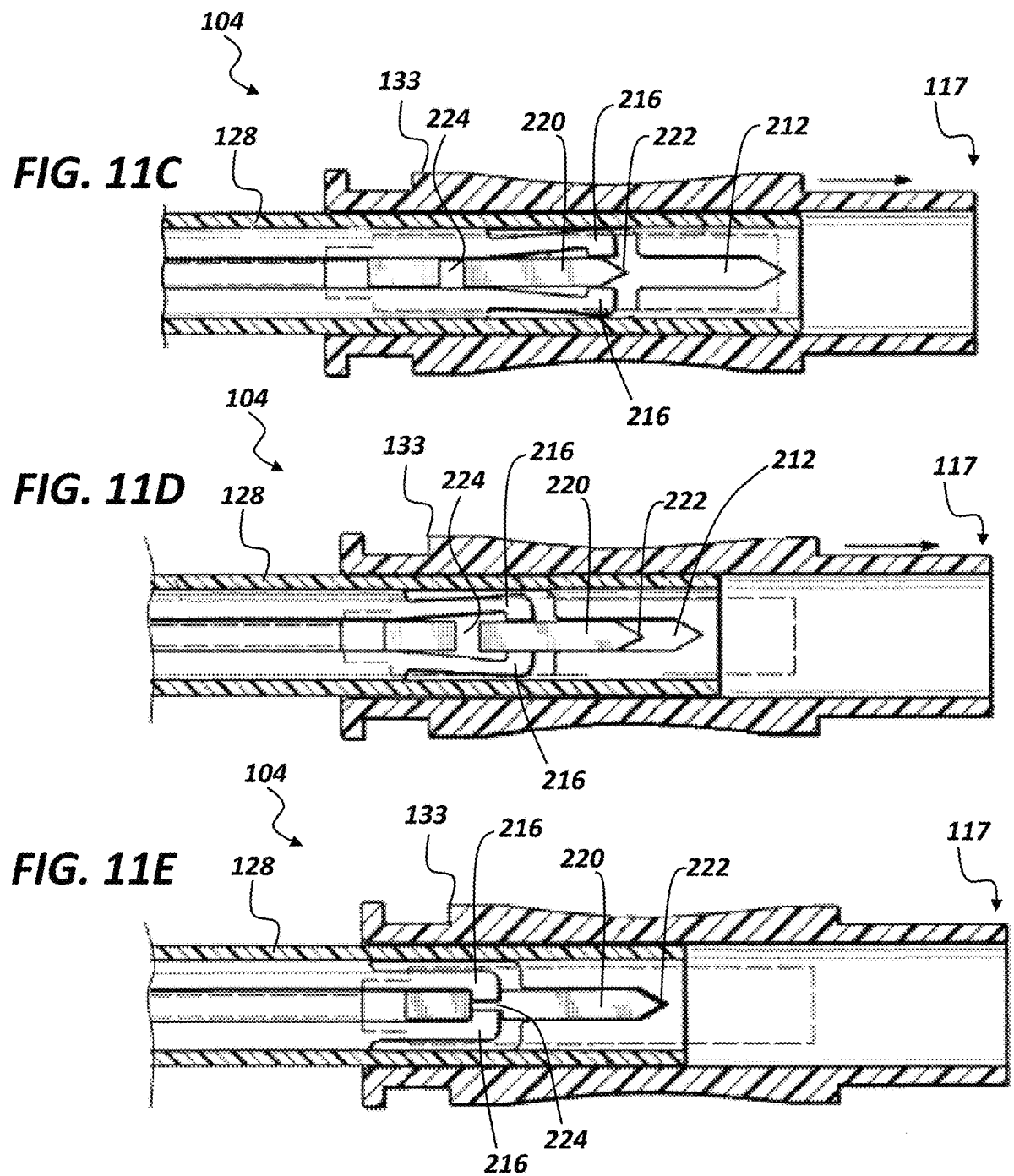

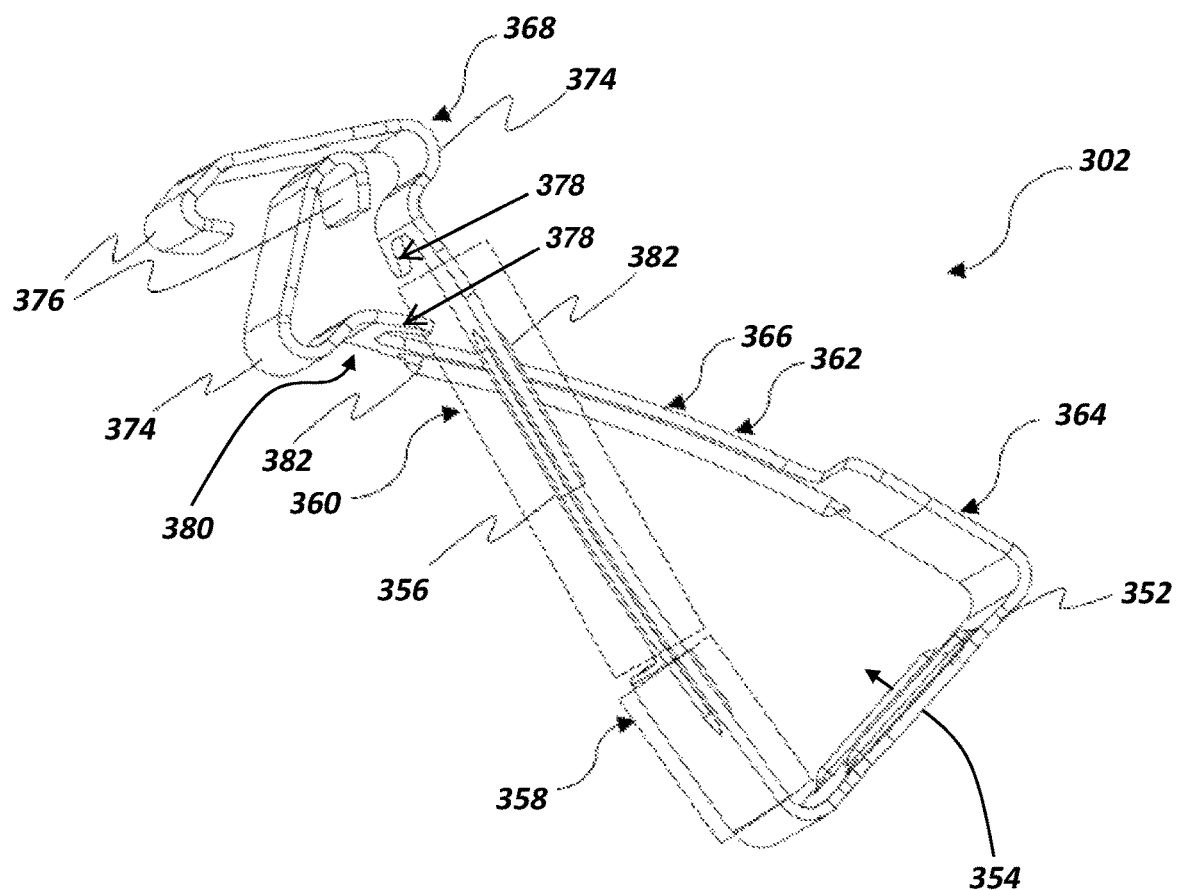
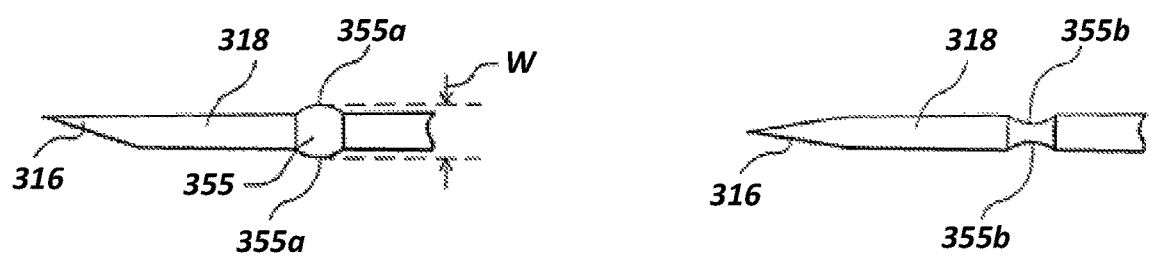
FIG. 16

INTRAVENOUS CANNULA

This application claims priority to Indian patent application Ser. No. 20/221,1002361, filed Jan. 14, 2022, entitled "INTRAVENOUS CANNULA," which is incorporated by reference herein, in the entirety and for all purposes.

TECHNICAL FIELD

The present disclosure relates to medical devices. Implementations include intravenous cannulas configured to prevent needle stick injuries. Implementations also include intravenous cannulas configured to prevent unintentional backflow of blood. Implementations also include intravenous cannulas equipped with improved catheter coupling and release mechanisms configured to facilitate reliable, safe disengagement of a catheter assembly from a needle guard assembly after placement of a distal end of the catheter assembly within a targeted blood vessel.

BACKGROUND

Intravenous cannulas are used to inject and/or withdraw fluids, such as medication, nutrients, or blood, directly into or out of a blood vessel of a patient. Intravenous cannulas typically include a catheter assembly and a needle insertion or protection assembly. A distal portion of a catheter tube included within the catheter assembly can be introduced into a blood vessel using a needle, after which the cannula may be secured to a patient's skin, for example, with an adhesive, which could be tape. The catheter tube included within such devices generally defines a lumen sized to accommodate insertion and retraction of a disposable hollow-bore needle therethrough. For this reason, the devices are occasionally referred to as over-the-needle cannulas.

When a distal portion of a catheter is inserted into a patient's vasculature, the disposable needle passing through the catheter is extended distally to puncture the patient's vein or artery, thereby providing an access point for the cannula to deliver or withdraw the desired fluid(s). The needle is then withdrawn, leaving the catheter assembly in place as a hub, which can be used, for example, for connections to various external hook-ups, e.g., fluid bottles. The catheter hub can also be capped for later use.

Despite their widespread and long-time use, preexisting intravenous cannulas remain problematic on multiple fronts. For example, cannulas often lack the safety features necessary to prevent catheter needles from injuring medical professionals before or after the distal tip of the needle is inserted into a patient's vasculature. Because of the high prevalence of communicable diseases among hospitalized patients in need of catheter-based treatments, the consequences of inadvertent needle pricks can be severe.

Cannulas have been designed to solve this problem by enclosing a portion of the needle within a needle guard housing moveable relative to an elongated needle tube, which may be sized to accommodate the full length of the needle before and after its deployment within a patient's vasculature. The elongated needle tube may constitute a component of a needle insertion assembly, which can be temporarily coupled to a catheter assembly, such that, after a distal portion of the catheter has been placed in a blood vessel, the needle can be withdrawn into the elongated needle tube and the needle insertion assembly disengaged from the catheter assembly. Devices configured in this manner are vulnerable to untimely separation of the catheter assembly from the needle insertion assembly, however, as they often rely entirely on sufficient but not excessive friction for coupling the two components.

Another deficiency associated with the use of preexisting over-the-needle cannulas is that, upon withdrawal of the associated needles, an open channel within the cannula often remains, through which blood can drain and spill from the patient. Aside from excessive blood loss, such backflow and spillage further increases the risk of infection for medical professionals. Blood spillage resulting from uncontrolled backflow creates unhygienic conditions, at least, for both the patient and medical personnel.

Preexisting approaches to minimizing blood spillage fail to minimize these risks and/or are unduly cumbersome to implement. For example, medical personnel may manually apply pressure near the needle insertion site before withdrawal of the needle to reduce the flow of blood, but this method requires skillful implementation of either a difficult two-hand technique executed by a single operator or the involvement of two operators. Both approaches may ultimately fail to prevent the undesirable flow of blood back through the catheter. Closed system intravenous cannulas are occasionally used to stop this unwanted backflow by positioning a dead stopper in the path of the blood flow and an angled side port to allow air escape for flashback visualization and fluid infusion; however, these devices are bulky, complicated to use, and more expensive than most standard products.

Indian patent application number 3031/DEL/2014 (hereinafter referred to as the '3031 patent application) provides another example of a preexisting, but imperfect, catheter device. One problem associated with the device disclosed therein is that, when the needle is retracted from the needle cover, the needle cover does not disengage from the catheter hub, meaning more force is required to disengage the needle cover from the catheter hub. Still further, the needle disclosed in the '3031 patent application does not engage the needle cover with the catheter hub, which impedes the overall functionality of the catheter. This defect forces operators to manipulate the catheter device to extract the needle cover from the hub, which in turn may damage the targeted blood vessel and cause pain.

Other preexisting products and methods utilize a mandrel or obturator to physically block unwanted blood flow, but again, these approaches require enhanced skill and training, and the required devices are typically expensive and complex in structure.

The present disclosure is directed to improved cannulas designed to overcome the aforementioned problems in addition to providing other technical advantages.

SUMMARY OF THE DISCLOSURE

One object of present disclosure is to provide an intravenous cannula device configured to prevent reverse flow of blood.

Another object of present disclosure is to provide an intravenous cannula device with a novel one-way valve design configured to prevent the reverse flow of blood.

Another object of present disclosure is to provide a mechanism for preventing reverse flow of blood that may be applied to a variety of catheter devices.

Another object of the present disclosure is to prevent needle prick injuries that may be sustained by a medical professional before or after puncturing a vein or artery of a patient.

Embodiments of the intravenous cannula devices described herein can include a catheter assembly configured to couple with a needle guard assembly, where both components are configured to accommodate the passage of a needle therethrough. Embodiments of the catheter assembly can include a catheter hub having a proximal end and a distal end, a coaxial recess with an annular stopper disposed at or near the proximal end of the catheter hub, and an undercut portion disposed at or near the distal end of the catheter hub. "Coaxial" refers to a tube in a tube, with their axes running the same direction; the axes in a coaxial arrangement may be, but need not be, coincident.

Embodiments can further include a valve member configured to be disposed inside the coaxial recess of the catheter hub. The valve member can define a cylindrical portion and a flat or curved portion disposed at one end of the cylindrical portion, and a coaxial recess extending from the cylindrical portion to the curved or flat portion. The flat or curved portion can include one or more slits defining a plurality of prongs through which a needle can pass to facilitate the puncturing of a blood vessel of a patient.

Embodiments of cannula devices can include a flashback chamber configured to receive proximally flowing blood indicative of successfully puncturing a targeted blood vessel by the needle extending distally from the cannula. Cannula devices disclosed herein can also include an actuator member having an axial bore. The actuator member can be configured to be disposed within the coaxial recess of the valve member, where it can open the plurality of prongs of the valve member to form a passage for a fluid flow from the proximal end of the catheter hub to the distal end of the catheter hub when a luer lock member is removably connected at the proximal end of the catheter hub abutting the actuator member.

Embodiments can also include a valve closure member having a first surface at a proximal end, a second surface at a distal end, and a through-hole extending between the proximal end and the distal end. The valve closure member can be disposed within the catheter hub such that the first surface of the valve closure member abuts the undercut portion of the catheter hub and the second surface of the valve closure member abuts the curved or flat portion of the valve member. The valve closure member can be configured to close the plurality of prongs of the valve member, thereby closing the passage for fluid flow and preventing blood flow from the punctured blood vessel of the patient from the distal end of the catheter hub to the proximal end of the catheter hub when the luer lock member abutting the actuator member is removed.

In some embodiments, the valve closure member can have a hardness ranging from about 50 Shore to about 80 Shore, and the valve member can have a hardness ranging from about 20 Shore to about 45 Shore. The disparity in hardness values between the valve closure member and valve member can facilitate closing of the valve member by the valve closure member when a needle is not present within the members.

In some embodiments, the shape of the first surface of the valve closure member can be curved, concave, or frustoconical. In some embodiments, the first surface of the valve closure member can have a flat or substantially flat shape. The shape of the first surface of the valve closure member may be complementary to the distal surface of the valve member. Any suitable shape may be used.

In some embodiments, the surface of the valve member defining the slit(s) can be convex or frustoconical. In some embodiments, the surface of the valve member defining the slit(s) can be flat or substantially flat. Any suitable shape may be used.

In some embodiments, the valve member can be configured to be held in place within the coaxial recess of the catheter hub when a first end of the valve member abuts an annular stopper within the catheter hub.

In some embodiments, the valve member can be made of a flexible material, non-limiting examples of which can include silicone, rubber, polymers, and/or Nitinol or other materials. Due at least in part to its flexible composition, the valve member can self-close after retraction of a needle proximally through the valve member.

In some embodiments, the slits defined by the valve member can form a Y-shape, an inverted Y-shape, an X-shape, a + shape, any other shape or orientation, or a combination thereof.

In some embodiments, the cylindrical portion of the valve member can have a protrusion at an inner surface thereof. In some embodiments, the actuator member can have a circular recess at an outer surface thereof. According to such embodiments, the protrusion of the valve member can be configured to engage with the circular recess of the actuator member, thereby forming an assembly comprised of the valve member and the actuator member inside the catheter hub.

In some embodiments, the actuator member can include a first end having a radially extending flange, a second end having a convex surface, and an axial bore extending between the first end and the second end. In some embodiments, the actuator member can include a first end having a radially extending flange, a second end having a flat or substantially flat surface, and an axial bore extending between the first end and the second end.

In some embodiments, the valve closure member can be harder than the plurality of prongs of the valve member such that when the luer lock member is disengaged from the catheter hub, the valve closure member pushes the plurality of prongs and the actuator member in a direction away from the distal end of the catheter hub, thereby preventing blood flow from the punctured blood vessel of the patient from the distal end of the catheter hub to the proximal end of the catheter hub.

In some embodiments, the actuator member can be made of a rigid material, including a rigid plastic or metal.

In some embodiments, the cannula device can include a flashback chamber having a porous filter and a cover to allow air to escape and blood to flow inside the flashback chamber.

In some embodiments, the device can include a needle prick safety device or component.

In some embodiments, the needle guard assembly can include an elongated tubular member and a needle hub comprising a needle holder disposed inside the elongated tubular member. A distal end of the needle holder can be connected to the needle configured to puncture a targeted blood vessel within a patient. Embodiments can also include a safety release component fixed or coupled to a distal end of the elongated tubular member. The safety release component can be configured to releasably couple with the catheter hub, thereby coupling the catheter assembly with the needle guard assembly. The safety release component can include one or more locking elements at or near its distal end, which can be configured to project and/or move radially outwardly when a needle is inserted within the safety release component. Outward projection and/or movement of the locking elements may cause them to fit within, and thus engage with, an annular groove defined by a proximal portion of the catheter hub, thereby forming a locking engagement and/or a tight fit relationship between needle guard assembly and the catheter assembly when the needle is passed through the safety release component to puncture a patient's blood vessel. When the needle is retracted through the catheter assembly and the safety release component after puncturing the patient's blood vessel, the locking elements retract, and/or can be displaced, from the annular groove of the catheter hub, thereby disengaging the safety release component and catheter hub. This disengagement allows separation of the catheter assembly from the needle guard assembly, but only when the needle is enclosed within the safety release component and needle guard assembly. In this manner, embodiments of the cannula devices disclosed herein can shield the distal tip of the needle upon its withdrawal from a patient to prevent inadvertent needle stick injuries.

In some embodiments, the safety release component can define a groove on an outer surface to accommodate the one or more locking elements.

In some embodiments, the one or more locking elements can be solid and spherical. The locking element(s) can also be made of a rigid or substantially rigid material, such as a metal, e.g., stainless steel and/or Nitinol and/or etc.

In some embodiments, the groove of the safety release component can have a diameter greater than or equal to a diameter of the locking element(s).

In some embodiments, the proximal end of the safety release component can have a circular base portion defining a central bore and fixed with the distal end of the elongated tubular member.

In some embodiments, the safety release component can include a tubular portion extending from the circular base portion and defining an axial bore configured to accommodate the passage of a needle to and from a targeted insertion site.

In some embodiments, the groove defined by the outer surface of the tubular portion of the safety release component can extend toward the axial bore of the safety release component.

In some embodiments, the solid spherical elements of the safety release component can be configured to extend outwardly to engage with the annular groove of the catheter hub, thereby forming the locking engagement and tight fit relationship between the elongated tubular member and the catheter assembly when a needle is passed through the safety release component pursuant to puncturing a blood vessel of a patient.

In some embodiments, when the needle is retracted proximally through the safety release component after puncturing the blood vessel of a patient, the locking elements of the safety release component decouple from the annular groove defined by the catheter hub, thereby disengaging the safety release component (and needle guard assembly) from the catheter assembly. Disengagement of the safety release component from the catheter assembly allows separation of the catheter assembly from the needle guard assembly, but only after the distal tip of the needle has been fully enclosed within the safety release component.

In some embodiments, the safety release component included in the needle guard assembly can include a safety clip. The safety clip may bias outwardly to engage at least one interlocking flange defined in a body portion of the needle guard assembly. Outward biasing of the safety clip can allow a needle member to extend through the needle guard assembly and catheter hub. Upon withdrawal of the needle member from the proximal end of the catheter hub, the safety clip may disengage from the interlocking flange and enclose a tip portion of the needle member within the safety clip, thereby reducing the likelihood of needle prick injuries upon withdrawal of the needle member from the catheter hub.

In some embodiments, the safety clip may comprise a bracket defining an opening for receiving the needle member. A first resilient arm may extend from one end of the bracket and may have a connecting portion for engaging with the at least one portion with the at least one interlocking flange of the body portion and needle member. The first resilient arm can comprise a first section and a second section. A second resilient arm can extend from an opposing end of the bracket and can further comprise a connecting portion for engaging with the at least one interlocking flange of the body portion and the needle member. The second resilient arm can also include a first section and a second section, and the dimensions of the first section can be larger than the second section. The connecting portion of each of the first and second resilient arms can be configured to engage with the interlocking flange and a body portion of the needle member when the needle member is extending through the catheter hub en route to puncturing a patient's blood vessel. The connecting portion can disengage from the interlocking flange and body of the needle member when the needle member is withdrawn from the proximal end of the catheter hub.

In some embodiments, the connecting portion of each of the first and second resilient arms includes a curved protrusion at one end. The curved protrusion can be configured to engage with the at least one interlocking flange of the body portion and a curved lip segment. The curved lip segment can extend inwardly toward the bracket member and can be configured to engage with the needle member. The curved lip can be configured to enclose the tip portion of the needle member within the safety clip when the needle member is withdrawn from the proximal end of the catheter hub.

In some embodiments, the curved protrusion includes a projection extending towards the bracket. The projection, together with the second section of the first and second resilient arms, can define a seat portion, which can be configured to receive and seat the tip portion of the needle member, thereby preventing misalignment of the needle member during withdrawal from the catheter hub.

In some embodiments, the first resilient arm can be longer than the second resilient arm.

In some embodiments, at least one of the bracket, the first resilient arm, and/or the second resilient arm can be defined with at least one rib member for reinforcement.

In some embodiments, the rib member can be disposed at a second section of the first and second resilient arms to reinforce the first and second resilient arms.

In some embodiments, each of the at least one interlocking flange of the body portion extends radially inwardly for ensuring engagement with the safety clip in its biased configuration, so that the safety clip is retained within the needle guard assembly.

In some embodiments, the needle member can include a protuberance proximal to its distal end. The protuberance can be configured to engage with the bracket during withdrawal of the needle member from the proximal end of the catheter tube, thereby preventing release of the needle member from the needle guard assembly.

Other features and aspects of this disclosure will be apparent from the following description and the accompanying drawings.

BRIEF DESCRIPTION OF THE DRAWINGS

FIG. 7A is a perspective view of an example of a valve closure member of the intravenous cannula device shown in FIGS. 1 and 2.

FIG. 7B is a cross-sectional view of the valve closure member shown in FIG. 7A.

FIG. 7C is a front view of the valve closure member shown in FIG. 7A.

FIG. 7D is a rear view of the valve closure member shown in FIG. 7A.

FIGS. 11A, 11B, 11C, 11D, and 11E are progressive snapshots of a portion of the needle guard assembly shown in FIG. 10 as the configuration of the needle guard assembly moves from an injection state to a shielded state.

FIG. 16 is a perspective view of a safety clip disposed within a needle guard assembly of the cannula device shown in FIG. 13 according to embodiments of the present disclosure.

DETAILED DESCRIPTION

Figure 1:
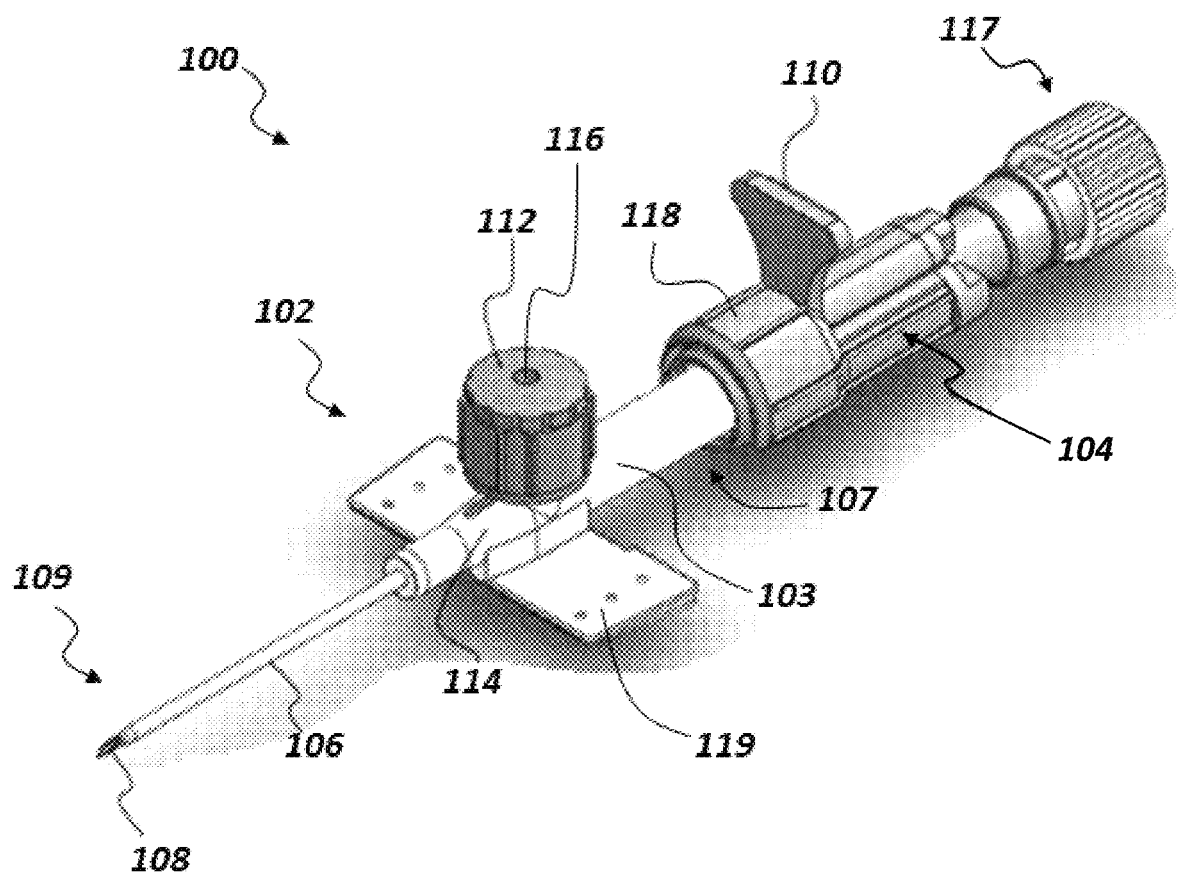
FIG. 1 is a perspective view of an example of an intravenous cannula device in accordance with embodiments of the present disclosure.

Provided herein are non-limiting embodiments of the present disclosure. References to specific embodiments and features are detailed throughout this disclosure, and examples are illustrated in the accompanying drawings. Reference numbers are included in the drawings to refer to the same or corresponding parts. References to various elements described herein are made collectively or individually when there may be more than one element of the same type; however, such references are merely exemplary in nature. Any reference to elements in singular form may also be construed to relate to plural form and vice-versa without limiting the scope of the disclosure to the exact number or type of such elements, unless set forth explicitly in the text.

As used herein, the term "proximal end" may refer to an end closer to the operator of a disclosed device. The term "distal end" as used herein may refer to an end opposite the "proximal end," which may be closer to the patient being treated by a disclosed device. Accordingly, the terms "distal" or "distal end" and "proximal" or "proximal end" may refer to directions or ends which are respectively further from and closer to the operator inserting a catheter into the body of a patient.

As used herein, the terms "operator" and "user" may be used interchangeably and may include, but are not limited to, medical professionals and personnel, such as nurses or para-medical staff who may work under the direction and supervision of doctors, physicians, and/or surgeons, who may also be considered users or operators according to the embodiments described herein.

The terms "connected" or "fixedly connected" as used in the present disclosure may refer to components that may be attached to each other in a fixed manner, which may be permanent in the sense that disconnection would require specialized tools and/or excessive physical force. "Releasably connected" or "coupled" may refer to components that may be temporarily connected and disconnected via one or more device features. The term "slidably connected" may refer to components assembled together in such a manner that any one or more of the components can slide relative to the other(s) during device employment. The contact surfaces of the components may enable such sliding. The term "disposed" used herein may mean that a component or element of a device may be connected to another element such that a workable assembly is formed without hindering the functionality of each individual element. The term "comprising" means that a given device or components thereof may include additional components apart from the components explicitly identified herein.

This disclosure includes numeric terms and phrases such as "one or more," "at least," "a," and "an." The specific numbers associated with such terms should not be construed as limiting.

Terms defining shapes, e.g., "convex," "frustoconical," "flat," "substantially flat," "cylindrical," "tubular," "extended," "circular," "converging," "diverging," "tapered," or "expanding" should also not be construed as limiting. A person of ordinary skill would recognize that these shapes allow for some variation, e.g., a "circular" shape, whether or not modified by a term such as "generally" or "substantially," need not meet the theoretical definition of "circular" to be circular within the meaning of the term as used herein. Other shapes may be possible in certain embodiments. As such, a person of ordinary skill in the art may develop other shapes or shape combinations that preserve the workability of a disclosed device. Any of such alterations may still be encompassed within the present disclosure without departing from the invention.

The terminology used in the present disclosure includes the words specifically mentioned, derivatives thereof, and words of similar import. The embodiments illustrated below are not intended to be exhaustive or to limit the invention to the precise form disclosed. These embodiments are chosen and described to best explain the principles of the invention and its application, its practical use, and to enable others skilled in the art to best utilize and develop the invention.

Figure 2:
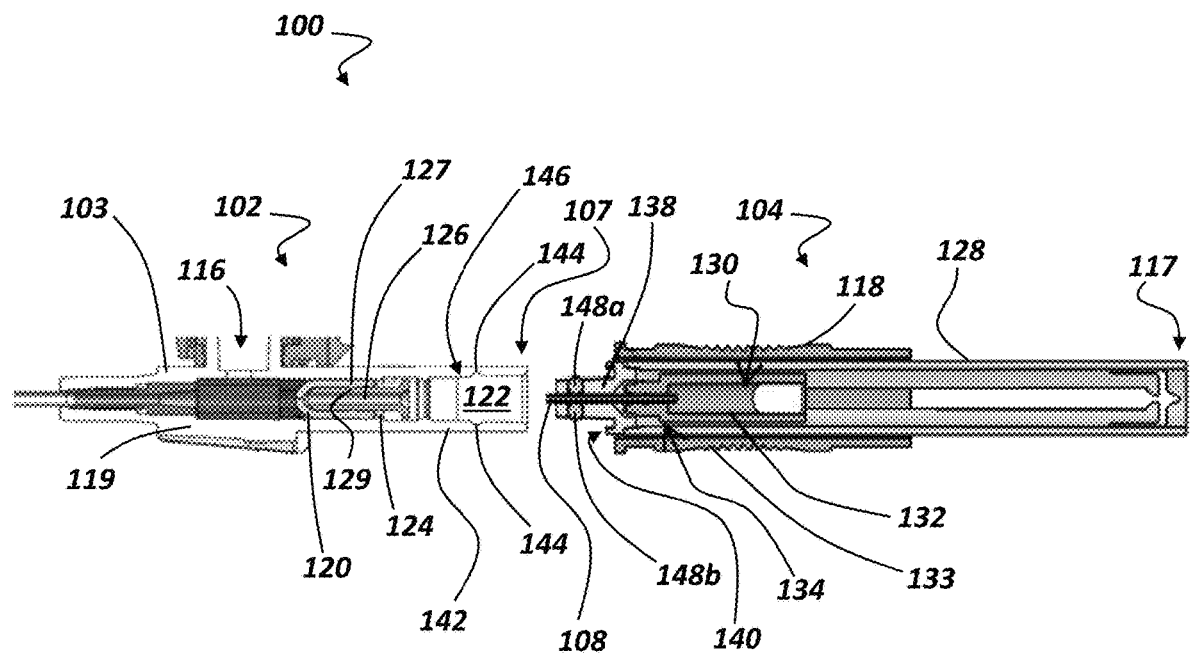
FIG. 2 is a cross-sectional view of the intravenous cannula device shown in FIG. 1.

FIGS. 1 and 2 illustrate a perspective view and a sectional view of a cannula 100, respectively, according to embodiments of the present disclosure. The illustrated cannula 100 is a medical device that can be used to administer a fluid medication via intravenous therapy and/or remove bodily fluids, e.g., blood, from a patient for subsequent analysis. The particular type of cannula device disclosed herein may vary, as can the associated tasks performed therewith. In the illustrated figures, the cannula 100 is an intravenous cannula device. The term "intravenous cannula" is used interchangeably with "cannula" herein for brevity.

The cannula 100 illustrated in FIGS. 1 and 2 includes a catheter assembly 102 configured to reversibly couple with a needle hub, chamber, or guard assembly 104. As shown in FIG. 1, the catheter assembly 102 may be coupled with the needle guard assembly 104, and, as shown in FIG. 2, the catheter assembly 102 can be detached from the needle guard assembly 104.

The catheter assembly 102 includes a catheter hub 103 fixed or coupled with a catheter tube 106. Opposite a proximal end 107 of the catheter hub 103, a needle 108 is shown projecting distally from a distal end 109 of the catheter tube 106, which can be made of a flexible or soft material, non-limiting examples of which may include a plastic or polymer composition. In embodiments, other components of the catheter assembly 102, such as the catheter hub 103, can be made of a biocompatible material, which can be substantially rigid. In some examples, the proximal end 107 of the catheter hub 103 may be attached to, integrally formed with, or otherwise coupled with a larger catheter body member, such that the body member defines a coaxial recess or bore together with the catheter hub 103. In such examples, the catheter body member may be directly coupled to the needle guard assembly 104 such that after coupling, the body member serves as a connector or adapter between the guard assembly 104 and the catheter assembly 102. For ease of illustration, the catheter hub 103 is referred to as a single component herein.

The cannula 100 is configured such that the catheter assembly 102 can be decoupled from the needle guard assembly 104 after the needle 108 pierces a targeted blood vessel and is retracted proximally through catheter assembly 102, thereby leaving at least a portion of the distal portion of the catheter assembly 102 within the blood vessel to facilitate the delivery and/or withdrawal of various medications and/or bodily fluids. As further described herein, embodiments of the cannula 100 can also be configured to prevent the backflow of blood after catheter placement via inclusion of a blood control valve therein. Embodiments of the cannula 100 also can be configured to prevent inadvertent needle prick injuries by fully enclosing the needle 108, including its distal tip, within the needle guard assembly 104 after piercing a targeted blood vessel.

The catheter tube 106 defines an elongated, longitudinal bore through which the needle 108 can slide. The catheter tube 106 can be fixed with the catheter assembly 102 by a number of methods including, but not limited to, press fitting, adhesive bonding, or any other suitable method. In some examples, the catheter tube 106 may be formed integrally with the catheter assembly 102. For gripping and manipulating the cannula 100 to reposition the catheter tube 106 during insertion and retraction of the needle 108, a thumb grip 110 can also be included.

In the illustrated embodiment, the catheter assembly 102 further includes a dispensing cap 112 abutting an outer surface 114 of the catheter hub 103. The dispensing cap 112 covers an outer port 116, which can be utilized as an auxiliary fluid pathway fluidly coupled with a coaxial recess of the catheter assembly 102. Accordingly, the intravenous cannula 100 can be adapted to have a two-way fluid mechanism. The dispensing cap 112 opens and closes the outer port 116 to allow the supply of a fluid. Such opening and closing can be implemented via a hinged or threaded mechanism in some examples.

Distal to the proximal end 117 of the needle guard assembly 104, a luer lock member 118 can be included, which may be releasably coupled to the catheter assembly 102, for example via complementary tapered portions. Any luer lock member of standard size or having the ISO standards which conforms with the catheter assembly 102 can be used in various embodiments. For example, the ISO standards ISO-80369-20 and ISO-80369-7 can be used for a luer lock member having a 6% universal taper. In additional embodiments, the luer lock member 118 may have other configurations or shapes, such as a luer slip.

As further shown in FIG. 1, one or more wing members 119 can be attached or integrally formed with the catheter hub 103. The wing member(s) 119 may aid in connecting or affixing the catheter assembly 102 to a patient's clothing or body part, e.g., a hand, after puncturing a vein or artery.

FIG. 2 is a cross-sectional view of the cannula 100 in which the catheter assembly 102 and needle guard assembly 104 are not currently coupled. As shown, the catheter assembly 102 can include a valve member 120 positioned inside a coaxial recess 122 of the catheter hub 103. The valve member 120 may be tubular in shape, and may be referred to herein as the tubular valve member 120, though other suitable configurations may be used. The tubular valve member 120 is configured to prevent or reduce the backflow of blood by closing after proximal retraction of the needle 108 therethrough. The catheter assembly 102 further includes an annular stopper 124 disposed within the coaxial recess 122, where it abuts an inner surface of the catheter hub 103. The tubular valve member 120 is adapted to be held in place within the coaxial recess 122 of the catheter assembly 102 via abutment of its proximal end with the annular stopper 124. In some examples, the tubular valve member 120 is made of a flexible material, such as silicone or rubber. The annular stopper 124 may be integral with, connected to, or discrete from the valve member 120.

Within an axial bore of the tubular valve member 120 is an actuator member 126. As further described herein, distal movement of the actuator member 126 contributes to the opening of the tubular valve member 120, which creates a passageway for fluid to flow distally through the catheter assembly 102. A protrusion 127 defined by the inner surface of the tubular valve member 120 facilitates coordinated movement between the tubular valve member 120 and the actuator member 126 by engaging with a complementary, annular recess 129 defined by an outer surface of the actuator member 126.

As further shown in FIG. 2, the needle guard assembly 104 can include an elongated tubular member 128 and a needle hub 130 comprising a needle holder 132. A guard assembly 104 gripping member or surface 133 may surround at least a portion of the elongated tubular member 128. The needle holder 132 is disposed inside the elongated tubular member 128, where a distal portion 134 of the needle holder 132 can be connected to the needle 108. The elongated tubular member 128 may be sized to accommodate the entire length of the needle 108, such that retraction of the needle 108 into the elongated tubular member 128 encloses and shields the distal tip of the needle 108. The shape of the elongated tubular member 128 may vary, and may be cylindrical, rectangular, or any other suitable configuration.

The needle guard assembly 104 also includes a safety release component 138 fixed to a distal end 140 of the elongated tubular member 128. The safety release component 138 can be releasably coupled to the catheter hub 103 of the catheter assembly 102, such that, after such coupling, the catheter assembly 102 is coupled to the needle guard assembly 104, with the safety release component 138 positioned between the proximal end 107 of the catheter hub 103 and the distal end 140 of the elongated tubular member 128.

To facilitate coupling of the catheter assembly 102 with the needle guard assembly 104, the catheter hub 103 includes a proximal cylindrical portion 142 defining an annular groove 144 at its inner surface 146. The annular groove 144 of the proximal cylindrical portion 142 is complementary to, and thus configured to engage with, one or more locking elements 148a,b of the safety release component 138. The locking elements 148a,b can be inserted within the annular groove 144 only when the safety release component 138 is inserted within the coaxial recess 122 of the proximal cylindrical portion 142 and the needle 108 has been inserted within the safety release component 138. By tightly mating with the catheter hub 103 upon insertion of the needle 108 therethrough, the safety release component 138 increases the catheter separation force, thereby reducing the likelihood of the catheter assembly 102 uncoupling from the needle guard assembly 104 while the needle 108 remains positioned within the catheter assembly 102, in whole or in part. Likewise, upon retraction of the needle 108 proximally through the catheter assembly 102, the safety release component 138, and into the needle guard assembly 104, the catheter release force is decreased significantly, such that detachment of the needle guard assembly 104 from the catheter assembly 102 requires a relatively small amount of force. This reduced catheter release force enables easy removal of the needle guard assembly 104 by an operator, which lessens the likelihood of perturbing the placement of the catheter assembly 102 within the patient. In the illustrated embodiment, the two locking elements 148a,b are solid and spherical, but embodiments are not limited to solid, spherical locking elements. In lieu of grooves, notches, a ridge, or protrusions may be used.

Figure 13:
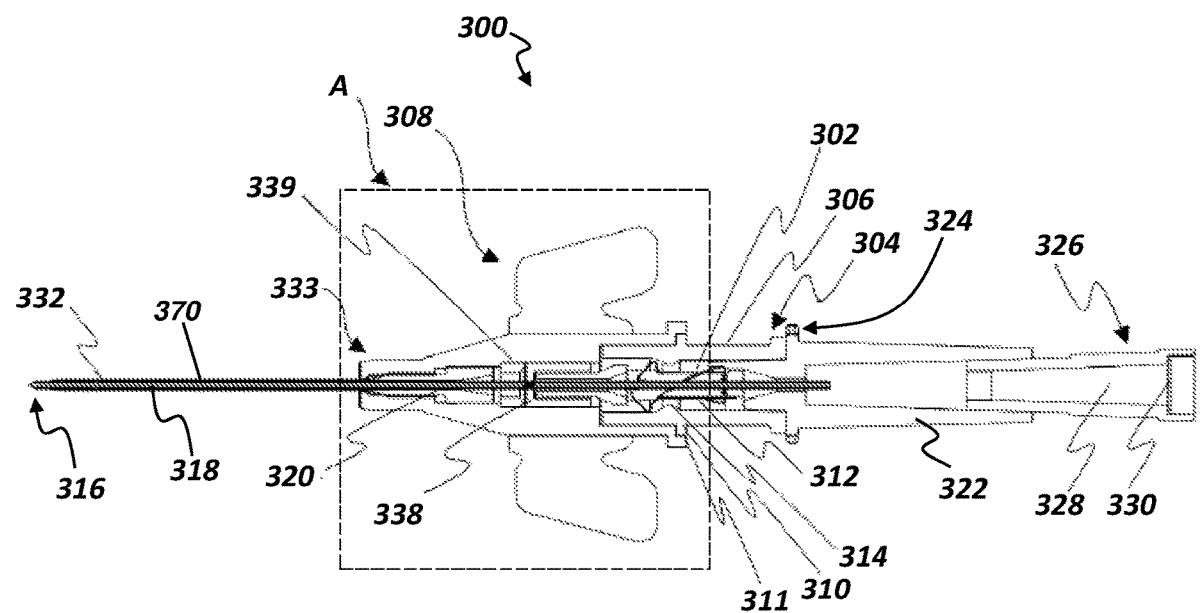
FIG. 13 is a cross-sectional view of another example of an intravenous cannula device in accordance with embodiments of the present disclosure.
Figure 14:
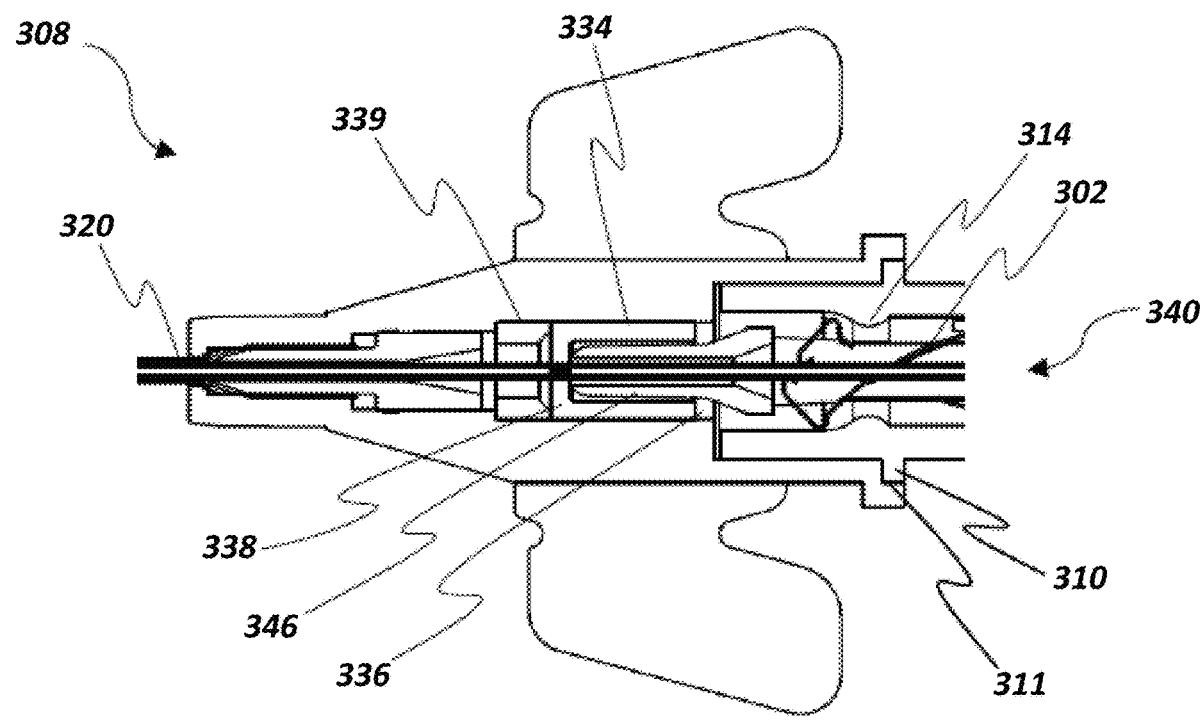
FIG. 14 is a magnified view of portion "A" depicting a catheter hub of the intravenous cannula device of FIG. 13.

The needle guard assembly 104 can also include or be coupled with a flashback chamber, an example of which is shown in FIG. 13. Blood flow into the flashback chamber from a patient confirms successful puncturing of a vein or artery by the needle 108. In embodiments, the needle hub 130 can serve as the flashback chamber. The needle hub 130 may also be telescopingly received within the elongated tubular member 128, such that the two components can move relative to each other.

Figure 3A:
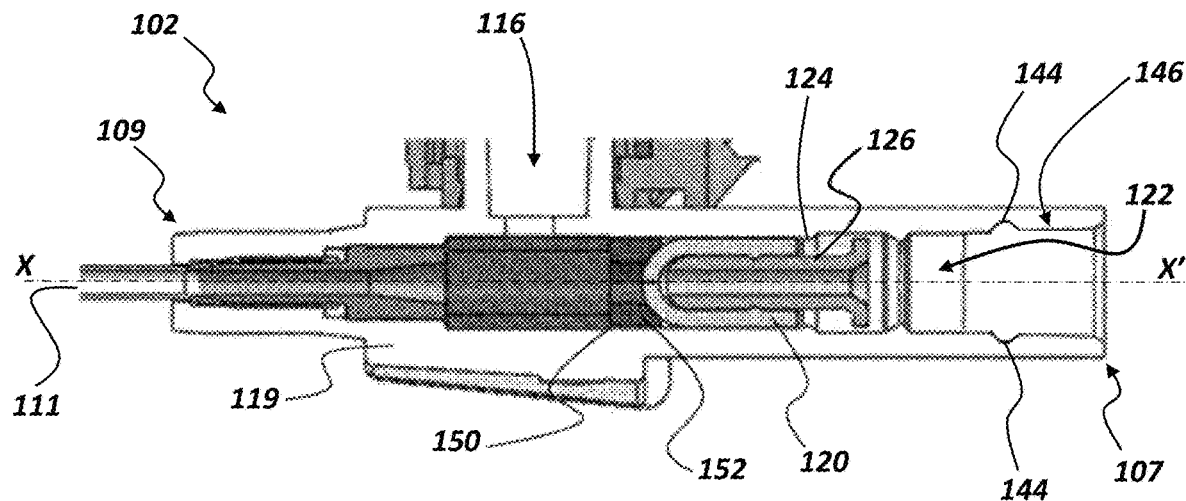
FIG. 3A is a magnified view of a catheter hub of the intravenous cannula device shown in FIGS. 1 and 2.

The magnified cross-sectional view of the catheter assembly 102 provided in FIG. 3A shows that the coaxial recess 122 of the catheter hub 103 can include an undercut portion 150 abutting a valve closure member 152. An inner bore 111 extends through the catheter hub 103 along the axis indicated from X' to X. In embodiments, a distal portion of the needle guard assembly 104, e.g., the safety release component 138, and/or a proximal portion of the catheter assembly 102, e.g., the proximal cylindrical portion 142, can include one or more radial seals configured to prevent entry and escape of fluids passing through or around the cannula 100.

Multiple components of the cannula 100 can be configured to collectively control the flow of bodily fluids and medication therethrough. With respect to the delivery of fluids to a patient, for example, engagement of the luer lock member 118 with the proximal cylindrical portion 142 of the catheter hub 103 generates a force on the actuator member 126 along the longitudinal axis of the catheter hub 103 toward the distal end 109 of the cannula 100. The safety release component 138 positioned at a distal end of the luer lock member 118 can be adapted to contact a proximal flange of the actuator member 126, such that the actuator member 126 is displaced axially toward the distal end 109 of the cannula 100. This axial displacement of the actuator member 126 opens a plurality of prongs of the tubular valve member 120 to form the fluid passage from a proximal end of the catheter hub 103 to the distal end 109 of the cannula 100 via an inner bore 111 of the catheter hub 103. In embodiments, the proximal cylindrical portion 142 of the catheter hub 103 can be a female luer fitting defined by a tapered open mouth, which is configured to receive the luer lock member 118 of the needle guard assembly 104.

Figure 3B:
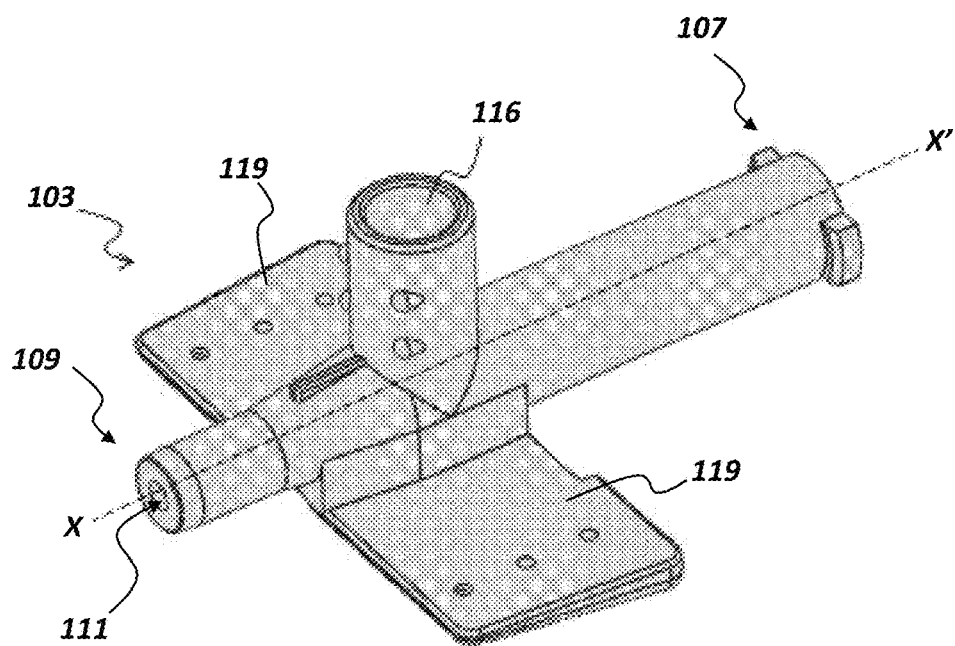
FIG. 3B is a perspective view of the catheter hub shown in FIG. 3A.

FIG. 3B illustrates a perspective view of the catheter hub 103, including its proximal end 107 and distal end 109. The inner bore 111 extends through the catheter hub 103 along the axis indicated from X' to X. In some embodiments, the catheter hub 103 can be made of a biocompatible material that is rigid and configured to secure each component coupled thereto.

Figure 4A:
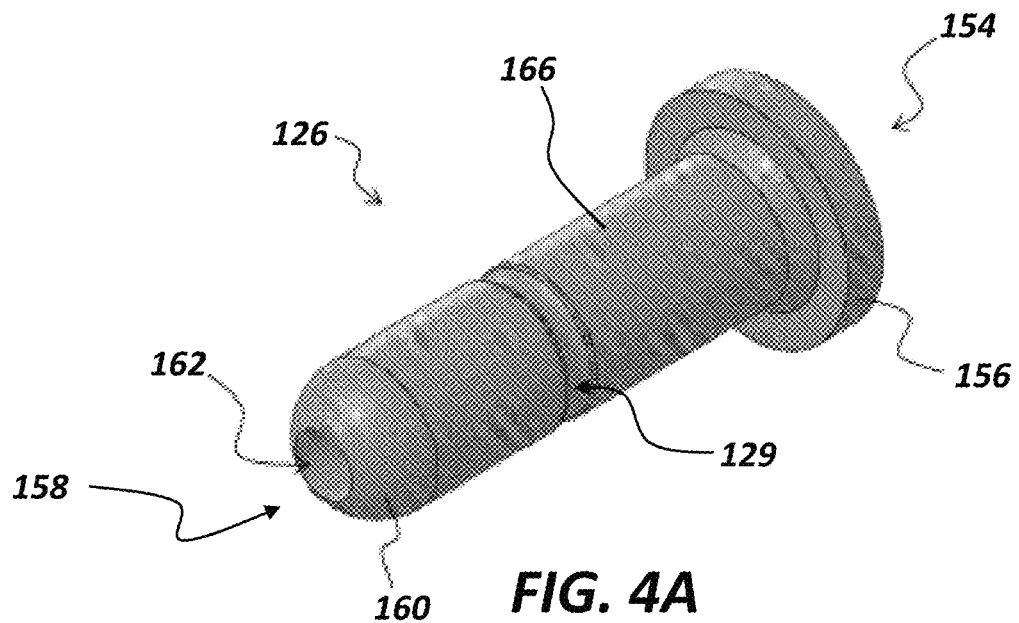
FIG. 4A is a perspective view of an example of an actuator member of the intravenous cannula device shown in FIGS. 1 and 2.
Figure 4B:
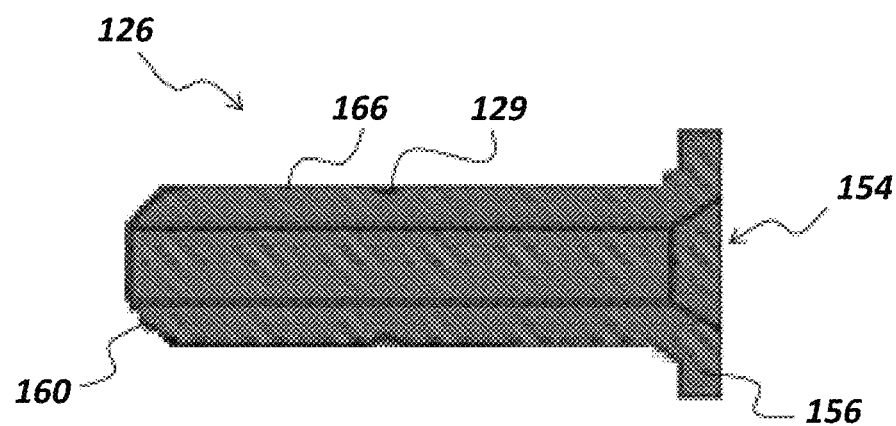
FIG. 4B is a cross-sectional view of the actuator member shown in FIG. 4A.

FIGS. 4A and 4B illustrate perspective and cross sectional views of an example of the actuator member 126 of the intravenous cannula 100. As shown, the actuator member 126 can include a proximal first end 154 having a radially extending flange 156, a distal second end 158 having a convex surface 160, and an axial bore 162 extending from the first end 154 to the second end 158. In embodiments, the actuator member 126 can be made of medical grade material such as, but not limited to, a rigid plastic material, e.g., polyoxymethylene (POM) or a metal, e.g., stainless steel or Nitinol.

As further shown in the illustrated embodiment, the actuator member 126 may also define an annular recess 129 extending around its outer surface 166. The annular recess 129 is complementary to the protrusion 127 defined by the tubular valve member 120, such that the protrusion 127 is configured to engage with the annular recess 129. Engagement of the protrusion 127 defined by the tubular valve member 120 with the annular recess 129 of the actuator member 126 can maintain the coupling of the tubular valve member 120 with the actuator member 126, thus forming an assembly inside the catheter hub 103 in which the two components move in unison and do not fall from the catheter hub 103. In additional or alternative embodiments, the tubular valve member 120 and the actuator member 126 may be connected by other mechanisms, such as a threaded connection or snap fit mechanism. In some examples, the actuator member 126 can include a protrusion similar to that of protrusion 127, and the tubular valve member 120 may include a recess similar to annular recess 129 of the actuator member 126. The annular recess 129 and protrusion 127 should therefore not be viewed as limiting.

The proximal flange 156 of the actuator member 126 can be configured to receive a force from the luer lock member 118 in the distal direction, which causes the actuator member 126 to move axially toward the distal end 109 of the cannula 100. Axial displacement of the actuator member 126 causes the tubular valve member 120 to open, thereby forming a fluid passageway from a proximal end of the catheter hub 103 to the distal end 109 of the cannula 100.

Figure 5A:
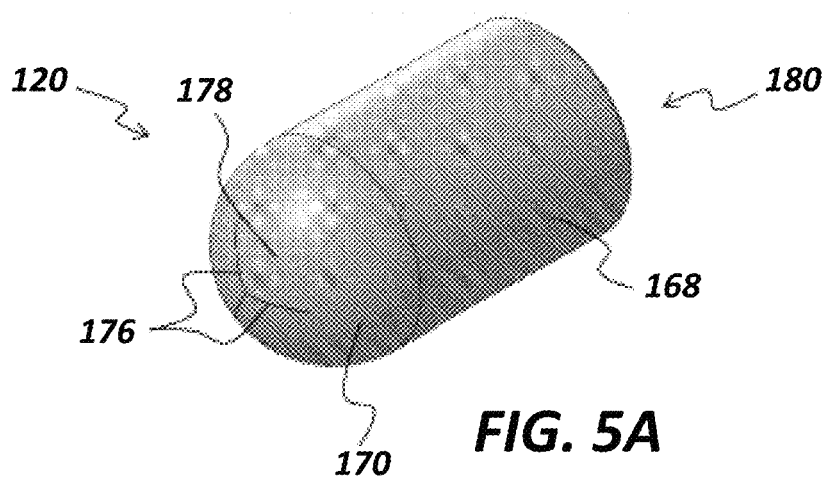
FIG. 5A is a perspective view of an example of a valve member of the intravenous cannula device shown in FIGS. 1 and 2.
Figure 5B:
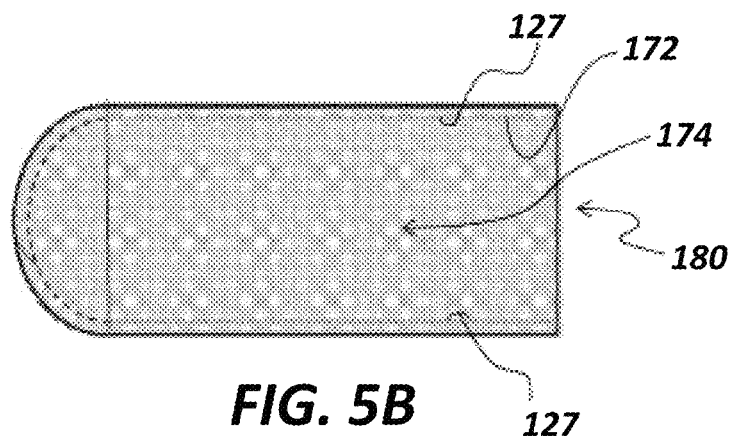
FIG. 5B is a cross-sectional view of the valve member shown in FIG. 5A.
Figure 5C:
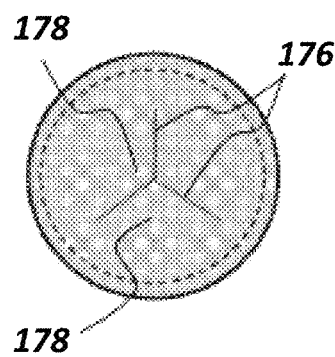
FIG. 5C is a front view of the valve member shown in FIG. 5A.
Figure 5D:
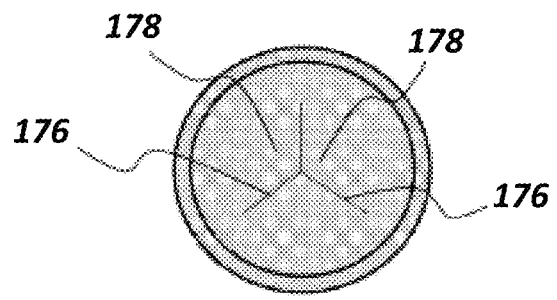
FIG. 5D is a rear view of the valve member shown in FIG. 5A.

An embodiment of the tubular valve member 120 is depicted in FIGS. 5A, 5B, 5C, and 5D. The tubular valve member 120, which can be made of a flexible material selected from a non-limiting group of materials comprising silicone and rubber, is configured to fit within the coaxial recess 122 of the catheter hub 103. In the example shown, the tubular valve member 120 is defined by a cylindrical portion 168 and a distal curved portion 170. The cylindrical portion 168 of the tubular valve member 120 defines the protrusion 127 at its inner surface 172, as shown in FIG. 5B. The tubular valve member 120 defines a recess 174 configured to accommodate the actuator member 126 extending from its cylindrical portion 168 to the distal curved portion 170. The recess may be coaxial and may be referred to herein as the coaxial recess 174. In the illustrated embodiment, the distal curved portion 170 is convex to mate with the complementary convex surface 160 of the actuator member 126 shown in FIGS. 4A and 4B; however, the curved portion 170 may also be other shapes, e.g., flat (or generally flat), frustoconical, or any other suitable shape. The terms "curved portion" and "convex portion" are used interchangeably herein, and they may relate to the same portion of the tubular valve member 120.

The convex portion 170 of the tubular valve member 120 includes one or more slits 176, which together define a plurality of prongs 178. The one or more slits 176 are designed to allow the needle 108 to pass therethrough and automatically close once the needle 108 is withdrawn, without the need for manually applied force. By self-healing in this manner, the slits 176 and prongs 178 of the convex distal surface 170 can prevent or minimize the backflow of blood through the tubular valve member 120, and thus the catheter assembly 102, when the needle 108 is withdrawn from the patient and retracted proximally through the coaxial recess 174 of the valve member 120. The slits 176 can comprise various shapes, non-limiting examples of which can include a Y-shape, an inverted Y-shape, an X-shape, a horizontal slit, a vertical slit, a "+" shape, or any combination thereof, or any other shape which will facilitate opening and expanding of the plurality of prongs 178 during the insertion of the needle 108 and the actuator member 126, respectively, inside the coaxial recess 174 of the tubular valve member 120.

In the illustrated embodiment, the tubular valve member 120 is configured to be held in place within the coaxial recess 122 of the catheter hub 103 when a first, proximal end 180 of the tubular valve member 120 abuts the annular stopper 124 of the catheter hub 103.

In operation, the needle 108 is passed through the coaxial recess 122 of the catheter hub 103 via the actuator member 126, after which the needle 108 can pierce the slits 176 of the tubular valve member 120. After passing through the slits 176 of the tubular valve member 120, the needle 108 passes through and beyond the catheter tube 106 for puncturing a blood vessel of a patient.

When the needle 108 is withdrawn after puncturing the blood vessel, the slits 176 of the tubular valve member 120 may close without user engagement because the tubular valve member 120 is made of flexible material configured to self-close the opening at the slits 176 of the convex portion 170 of the tubular valve member 120. Closure of the slits 176 can prevent the backflow of blood from the punctured blood vessel of a patient through the cannula such that after the needle 108 has been retracted and the catheter hub 103 released from the needle guard assembly 104, the catheter assembly 102 remains in the vasculature to provide an access port. In this manner, the tubular valve member 120 can prevent blood from coming out of the catheter hub 103 after implantation of the catheter tube 106 but before another component is attached to the catheter hub 103.

Figure 6A:
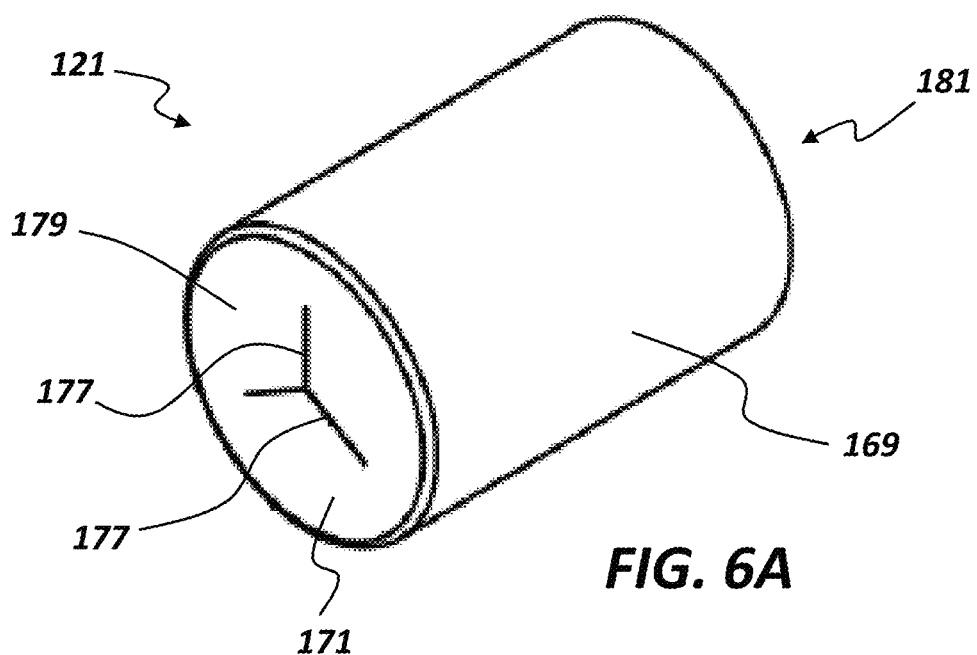
FIG. 6A is a perspective view of another example of a valve member of the intravenous cannula device shown in FIGS. 1 and 2.
Figure 6B:
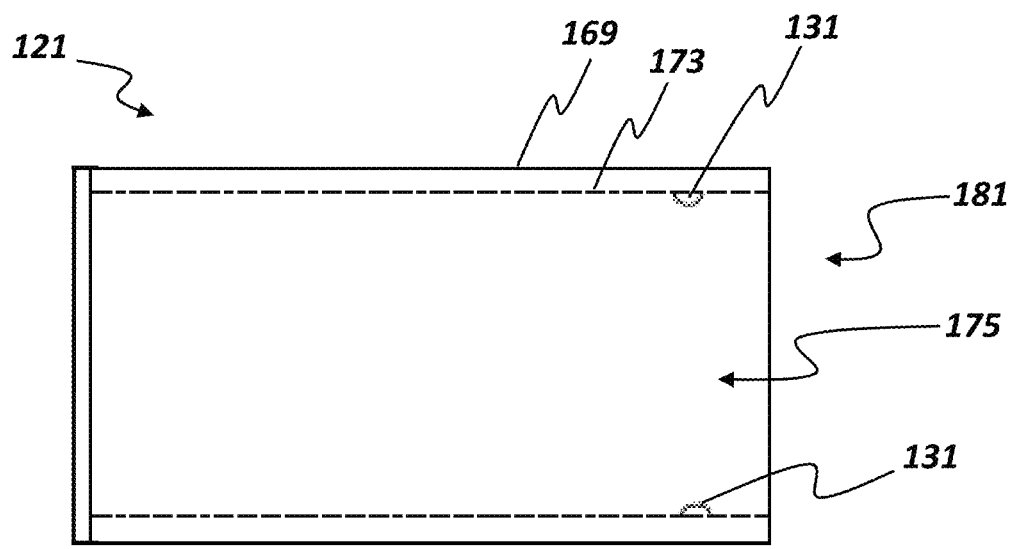
FIG. 6B is a cross-sectional view of the valve member shown in FIG. 6A.

The particular shape of the tubular valve member 120 may vary. For example, FIGS. 6A and 6B show a tubular valve member having a distal surface that is flat, or substantially flat. Like tubular valve member 120, the illustrated tubular valve member 121 is configured to be disposed within the coaxial recess 122 of the catheter hub 103. The tubular valve member 121 is defined by a cylindrical portion 169 having a protrusion 131 at its inner surface 173, which also defines a coaxial recess 175. Opposite its proximal end 181, the tubular valve member 121 has a flat distal surface 171, which like the convex distal surface 170 of tubular valve member 120, includes one or more slits 177 that together define a plurality of prongs 179. The one or more slits 177 are designed to allow the needle 108 to pass therethrough, and the slits 177 can close automatically without user manipulation once the needle 108 is withdrawn. By self-healing in this manner, the slits 177 and prongs 179 of the flat distal surface 171 can also prevent or minimize the backflow of blood through the tubular valve member 121, and thus the catheter assembly 102, when the needle 108 is withdrawn from a patient and retracted proximally through the coaxial recess 175 of the valve member 121.

FIGS. 7A, 7B, 7C, and 7D illustrate various views of an embodiment of the valve closure member 152 of the intravenous cannula 100. The valve closure member 152 includes a first surface 182 at its proximal end 184, a second surface 186 at its distal end 188, and a through-hole 190 extending from the proximal end 184 to the distal end 188. The valve closure member 152 can be disposed inside the catheter hub 103 such that the second surface 186 of the valve closure member 152 abuts the undercut portion 150 of the catheter hub 103 and the first surface 182 of the valve closure member 152 abuts the distal portion of the tubular valve member 120.

The valve closure member 152 can be configured to displace the prongs of the tubular valve member in a manner that closes or facilitates closing of the passage for fluid flow and prevents blood flow from the punctured blood vessel from the distal end 109 of the catheter tube 106 to the proximal end 107 of the catheter hub 103 when the luer lock member 118 abutting the actuator member 126 is removed.

In the illustrated embodiment, the valve closure member 152 is configured for use with tubular valve member 120, such that the convex portion 170 of the tubular valve member 120 conforms to the shape of the first surface 182 of the valve closure member 152. To accommodate differently shaped valve members, the valve closure member 152 may likewise have different shapes. For example, to accommodate tubular valve member 121, the first surface 182 of the valve closure member may be flat or substantially flat. The first surface 182 of the valve closure member 152 may also be convex, even when used together with distally flat tubular valve member 121. In non-limiting embodiments, the valve closure member 152 can have a hardness ranging from about 50 Shore to 80 Shore and the tubular valve member 120 can have a hardness ranging from about 20 Shore to 45 Shore. The plurality of prongs of the tubular valve member 120/121 can be more flexible relative to the valve closure member 152, such that the plurality of prongs 178/179 may close by returning to their resting state automatically or with the aid of the valve closure member 152 when the needle 108 is withdrawn after puncturing of a blood vessel.

The cannula 100 disclosed herein can thus prevent the backflow of blood after needle retraction via coordinated movement and interactions between a tubular valve member, an actuator member, and/or a valve closure member. Notably, the disclosed valve closure member and the actuator member may be repeatedly activated and de-activated without wearing, such that replacement of one or both components is not necessary, at least not frequently.

Figure 8:
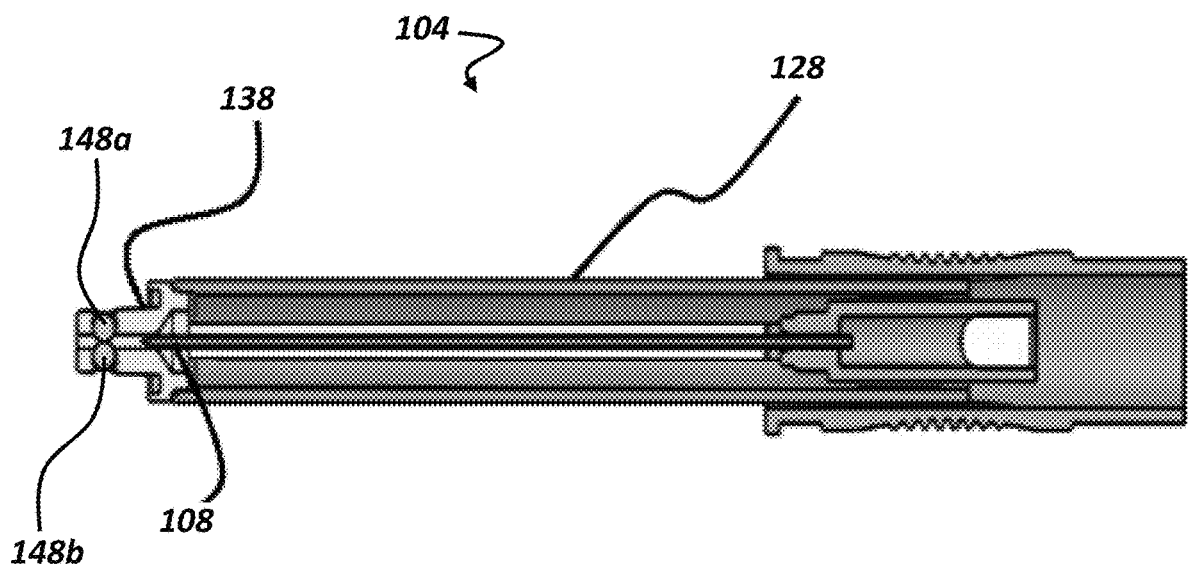
FIG. 8 is a cross-sectional view of an example of a configuration of a needle guard assembly of the intravenous cannula device shown in FIGS. 1 and 2 when a distal tip of a needle is enclosed within the needle guard assembly.

As noted herein, the cannula 100 can also include a needle prick prevention mechanism configured to enclose the distal tip of the needle 108 within the needle guard assembly 104 before and after insertion of the needle 108 within a patient. Safety release component 138, a cross section of which is shown in the needle guard assembly 104 depicted in FIG. 8, is an example of a component of a needle prick safety device implemented in accordance with embodiments disclosed herein. The safety release component 138 can include two moveable locking elements 148a,b configured to control the coupling of the catheter assembly 102 to the needle guard assembly 104 based on whether the needle 108 is present within either or both components. While FIG. 8 is shown with two moveable locking elements 148a,b, one, three, or more moveable locking elements may be used.

Figure 9A:
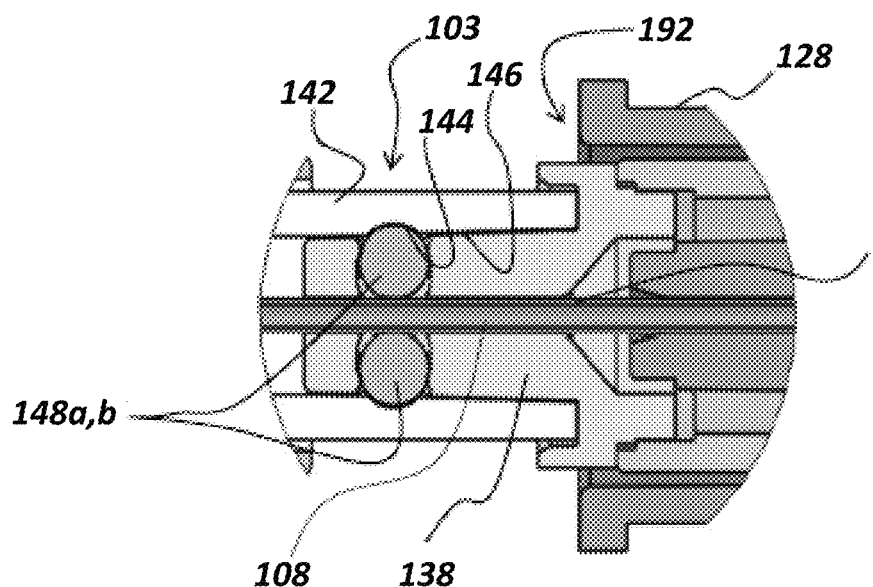
FIG. 9A is a cross-sectional view of an example of a safety release component coupled with a needle guard assembly in accordance with embodiments of the present disclosure.

FIG. 9A shows a close-up sectional view of the safety release component 138 and the surrounding features in an engaged, locked state with the proximal cylindrical portion 142 of the catheter hub 103. As shown, the locking elements 148a,b are each engaged or locked with a portion of the annular groove 144 defined by an inner surface 146 of the proximal cylindrical portion 142 of the catheter hub 103. In this engaged state, the safety release component 138 is fixed to a distal end 192 of the elongated tubular member 128 and releasably connected to the proximal cylindrical portion 142 of the catheter hub 103.

Figure 9B:
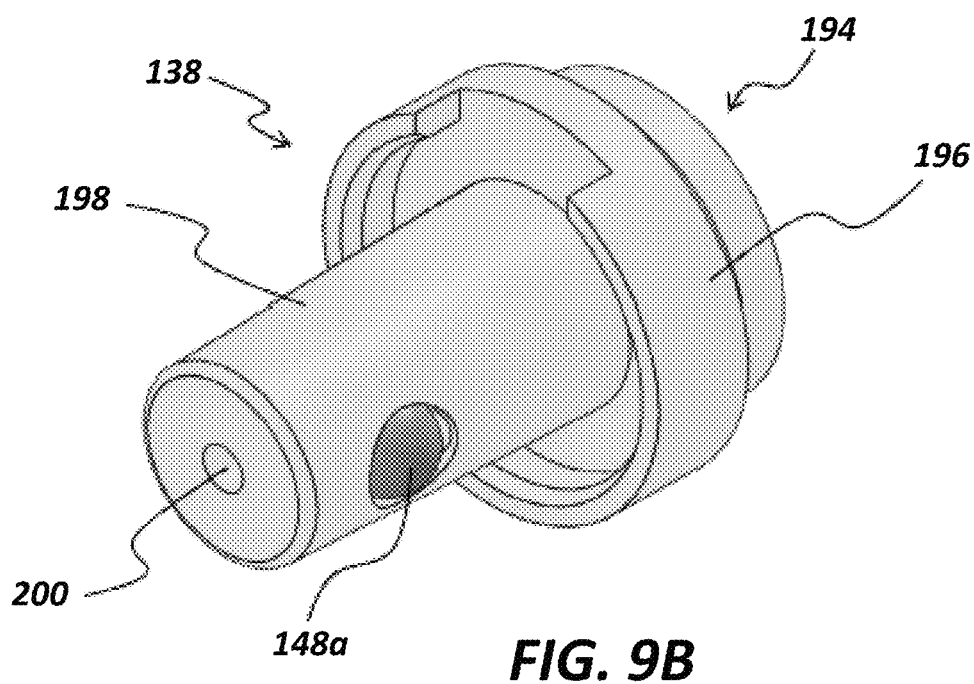
FIG. 9B is a perspective view of the safety release component shown in FIG. 9A.

FIG. 9B is a perspective view of the safety release component 138 according to embodiments disclosed herein. The safety release component 138 comprises a first, proximal end 194 having a circular base portion 196, which can be fixed to the distal end 192 of the elongated tubular member 128. In some examples, the circular base portion 196 can be press-fitted to the elongated tubular member 128, thereby unifying the two components. The safety release component 138 can also comprise a tubular portion 198 defining an axial bore 200 sized to accommodate passage of the needle 108 therethrough.

Figure 9C:
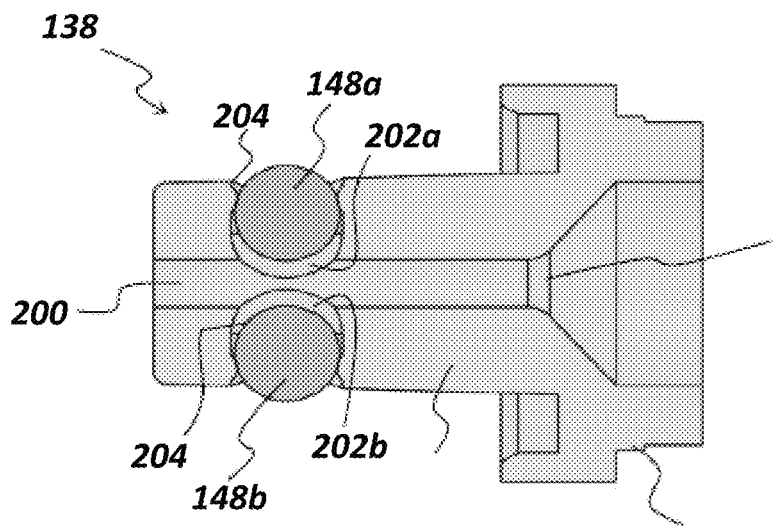
FIG. 9C is another cross-sectional view of the safety release component shown in FIG. 9A.
Figure 9D:
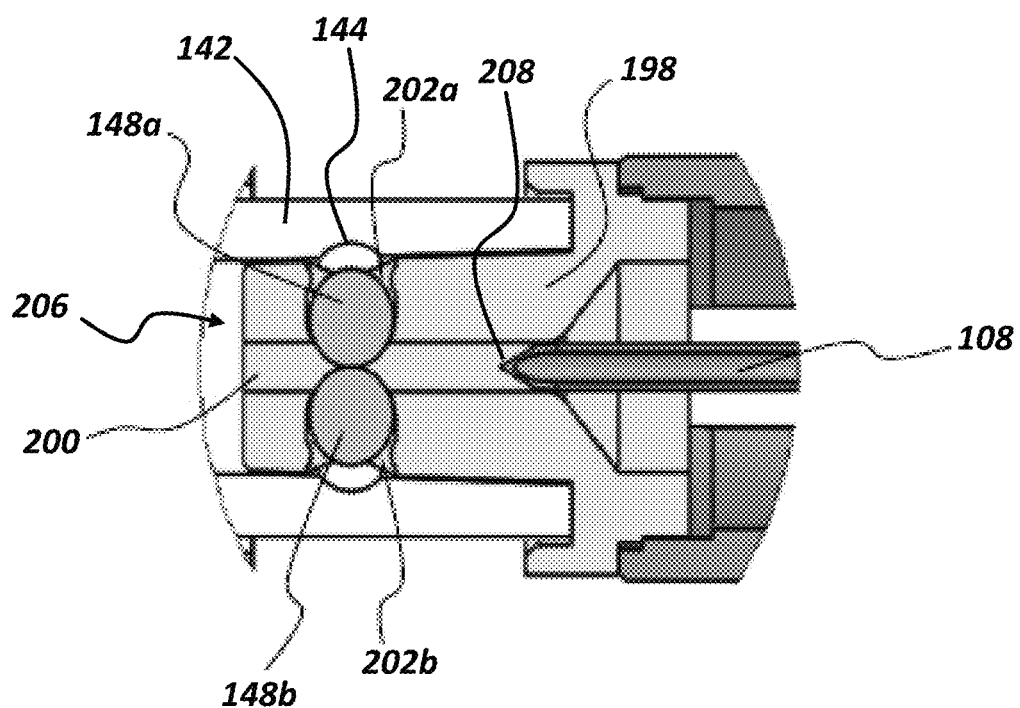
FIG. 9D is a cross-sectional view of an example of a configuration of the safety release component when a distal tip of a needle is enclosed within the needle safety component.

FIGS. 9C and 9D show the safety release component 138 in a disengaged or unlocked state relative to the catheter hub 103 at a snapshot in time during which the needle 108 is either being retracted proximally or extended distally, such that the needle tip 208 is momentarily positioned within the safety release component 138, where the tip is fully enclosed. The needle tip 208 is not yet fully withdrawn into the needle guard assembly 104, but is located in a safe, unexposed area within the safety release component 138 such that upon complete separation of the safety release component 138 (and needle guard assembly 104) from the catheter hub 103, the needle tip 208 may not cause accidental prick injuries. In the disengaged or unlocked state, the safety release component 138 may not be coupled with the catheter hub 103 or may at least not be locked with the catheter hub 103 but in the process of being separated therefrom, such that the safety release component 138 and needle guard assembly 104 to which it is attached may be readily separated in unison from the catheter assembly 102 by applying a small amount of tension force. As shown, the safety release component 138 can include one or more grooves 202a,b defined by the outer surface 204 of the tubular portion 198. Each of the grooves 202a,b is sized to accommodate one of locking elements 148a,b. The solid, spherical locking elements can be in the form of stainless steel balls, but the disclosed embodiments are not limited thereto. The locking elements may be any suitable shape, including but not limited to spherical, generally spherical, prolate spheroid, cylindrical (with or without tabs or other elements to keep the locking elements in the grooves 202a, b), conical, etc. The locking elements may be disconnected from and/or floating within the grooves, and/or they may be connected to or integral with the grooves, such as a shape tethered to a groove.

The diameter of each groove 202a,b can be substantially the same, or slightly greater, as the diameter of each corresponding locking element 148a,b. The size of each groove 202a,b facilitates smooth movement of the locking elements 148a,b radially outward when the needle 108 is passed through the axial bore 200 pursuant to puncturing a vein or artery, and radially inward after the subsequent withdrawal of the needle 108 from the patient and proximally through the safety release component 138.

Figure 10:
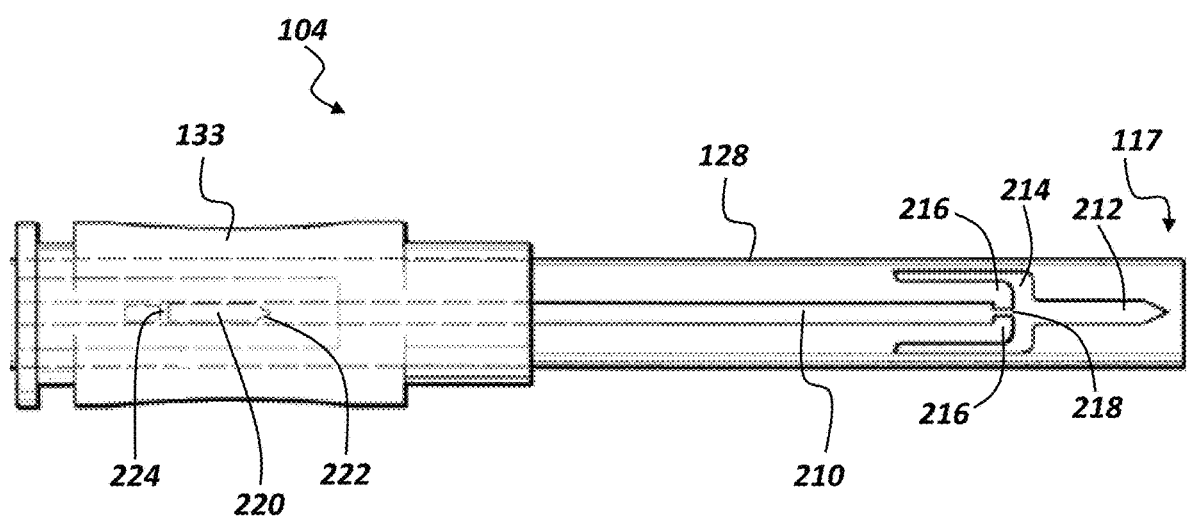
FIG. 10 is a cross-sectional view of an example of a needle guard assembly in accordance with embodiments of the present disclosure.

The locking elements 148a,b of the safety release component 138 are configured to engage with the annular groove 144 of the catheter hub 103, thereby forming a locking, tight-fit engagement between the elongated tubular member 128 of the needle guard assembly 104 and the catheter assembly 102 when the needle 108 is passed through the safety release component 138 for puncturing a vein or artery of a patient. The needle 108 thus displaces the locking elements 148a,b away from the axial bore 200 and into the annular groove 144 to lock the catheter assembly 102 to the needle guard assembly 104. FIG. 9D shows that, after withdrawing the needle 108 from the patient, through the catheter assembly 102, and proximal to a distal end 206 of the needle guard assembly 104, a distal tip 208 of the needle 108 can be nested within the safety release component 138, at which time the locking engagement between the catheter hub 103 and needle guard assembly can be released. The disengagement occurs because the locking elements 148a,b are able to be displaced inwardly, after retraction of the needle, from the annular groove 144 of the proximal cylindrical portion 142 of the catheter hub 103, thereby disengaging the locking engagement between the elongated tubular member 128 and the catheter assembly 102. Separation of the safety release component 138 from the catheter assembly 102 after nesting the needle tip 208 within the safety release component 138 allows the needle 108 to be withdrawn from a patient and removed from the catheter assembly 102 only when its distal tip 208 is concealed, thereby reducing the likelihood of needle prick injuries Embodiments of the cannulas described herein can also include a mechanism for ensuring safe, reliable locking and unlocking of the needle guard assembly 104 in a manner that further reduces the likelihood of needle prick injuries. FIG. 10 is a cross-sectional view of an example of a portion of the needle guard assembly 104 configured in this manner. As shown, the interior of the needle guard assembly 104 can include a longitudinal notch 210 defining a proximal receiving area 212. The notch 210 may further define a U-shaped slot detent cutout or notch 214, which defines a pair of fingers 216. Together, the fingers 216 define a narrow slot 218. The fingers 216 can be configured to be urged away from each other to widen the slot 218 pursuant to locking the needle guard assembly 104.

As illustrated together with FIG. 2, the needle guard assembly 104 may be configured to have an injection position, in which the needle 108 extends beyond the distal end 140 of the needle guard assembly 104, and a shielded position in which the distal tip 208 of the needle 108 is positioned proximal to the distal end 140, nestled within the needle guard assembly 104. To move the needle hub 130 from the injection position to the shielded position, the luer lock member 118 can be moved proximally, such that a projection or rib 220 also included within the needle guard assembly 104 moves proximally through the longitudinal notch 210.

The proximal end of the rib 220 can define a ramp or camming surface 222. In a resting state, i.e., before passage of the rib 220 therethrough, the slot 218 defined by the fingers 216 can be more narrow than the width or thickness of the rib 220. As the needle hub 130 is moved proximally toward the shielded position, the camming surface 222 of the rib 220 engages the fingers 216 and urges them apart, thereby widening the slot 218 to allow passage of the rib 220 therethrough. Proximal movement of the rib 220 through the longitudinal notch 210 and beyond the fingers 216 is shown progressively in FIGS. 11A, 11B, 11C, and 11D.

As the fingers 216 are urged apart, the needle hub 130 enters a lock actuation stage in which the force generated by the camming action of the camming surface 222 against the fingers 216 exerts increased resistance to movement of the needle hub 130. Entry into the lock actuation stage is shown in FIG. 11B and passage through the lock actuation stage is shown in FIG. 11C.

After the fingers 216 are urged apart to the extent necessary for the rib 220 to enter the slot 218, the total force acting against the movement of the rib 220 is exerted by the sliding action of the fingers 216 against the rib 220. This force decreases with continued proximal movement of the needle hub 130, and thus the rib 220, toward the shielded state, which is illustrated in FIGS. 11D and 11E.

Continued proximal movement of the needle hub 130 moves the rib gap 224 beyond the proximal end of the fingers 216, thereby allowing the fingers 216 to snap back to their original non-flexed state in which the ends of the fingers 216 settle within the rib gap 224. This configuration defines the locked, shielded state in which the needle 108 cannot be pushed distally without a high external force applied in the distal direction. To prevent additional proximal movement of the needle hub 130 relative to the elongated tubular member 128, the camming surface 222 can extend to and contact the proximal end of the receiving area 212.

Figure 12:
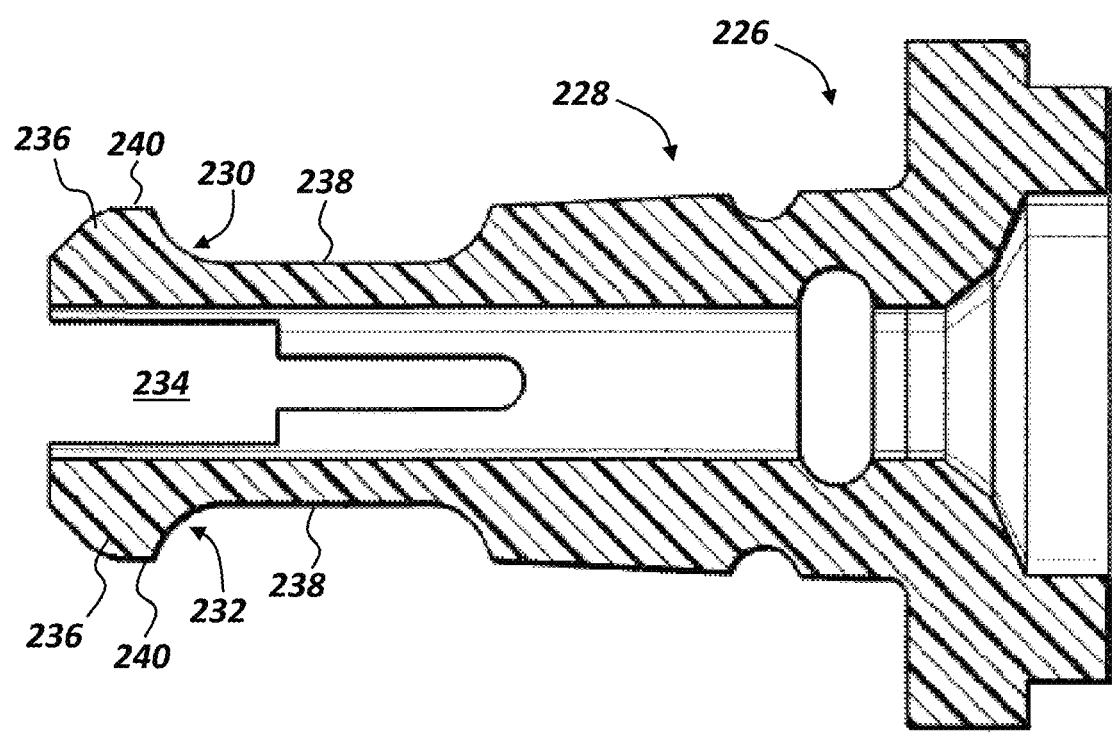
FIG. 12 is a cross-sectional view of an example of a duckbill component configured to releasably couple a catheter assembly to a needle guard assembly in accordance with embodiments of the present disclosure.

In some examples, the cannula 100 can additionally or alternatively include a duckbill release mechanism at the distal end 140 of the needle guard assembly 104, an example of which is shown in FIG. 12. As shown, the duckbill release mechanism can include a pair of cooperating members, e.g., arms, each extending distally from the distal end 140 of the needle guard assembly 104. The arms can be included in lieu of the moveable locking elements 148a,b of the safety release component 138 disclosed herein. Like the safety release component 138, the arms can be sized to fit within the proximal cylindrical portion 142 of the catheter hub 103. The forces exerted upon entry into the lock actuation stage described in connection with FIGS. 11A-11D can be exerted while the duckbill release mechanism secures the needle guard assembly 104 to the catheter insertion assembly 102. The safety release component 138 and duckbill release mechanism may be included in separate embodiments, such that the two release mechanisms are not included in the same cannula.

The cooperating arms can define a passageway therebetween configured to slidably receive the needle 108. One or both of the members may have a holding portion, such as a radially outward-protruding detent and/or radially inward extending recess configured for coupling with a complementary feature of the catheter hub 103, which may be defined by the inner surface 146 of the proximal cylindrical portion 142. Inclusion of the duckbill mechanism can ensure a strong coupling of the catheter assembly 102 with the needle guard assembly 104 when the needle 108 has been inserted therethrough. The duckbill mechanism may facilitate easy uncoupling of the catheter assembly 102 from the needle guard assembly 104 when the needle 108 is not present.

With reference again to FIG. 12, an example of a duckbill mechanism included in some embodiments can include a distal cap 226 comprised of a nose 228 configured to be removably coupled with the proximal cylindrical portion 142 of the catheter hub 103, such that the distal cap 226 abuts the inner surface 146 of the proximal cylindrical portion 142. A pair of distally extending arms 230, 232 defining a split cylinder are also sized to fit within the coaxial recess 122 of the catheter hub 103. The arms 230, 232 can flex radially toward each other upon receiving a compression force, but in the uncompressed, relaxed state, they can define a passageway 234 therebetween configured to slidably receive the needle 108. Alternatively, the arms 230, 232 can be biased inwardly toward one another and pushed into a parallel configuration when the needle is between them. The end of one or each arm 230, 232 can include a holding portion in the form of a protrusion or detent 236. The inclusion of one or more detents 236 defines one or more recesses 238 proximal thereto. The outer periphery 240 of the detents 236 can define an annular ring having a diameter that is at least slightly larger than the inner diameter of the proximal cylindrical portion 142 of the catheter hub 103. In some examples, the detents 236 may be distally chamfered.

When the needle 108 is present in the passageway 234 between the arms 230, 232, compression of the arms 230, 232 is impeded such that uncoupling of the distal cap 226 from the coaxial recess 122 of the catheter hub 103 requires considerable force, thereby reducing the likelihood of the catheter assembly 102 separating from the needle guard assembly 104 when the needle 108 remains within the catheter assembly 102. Alternatively, when the arms are biased toward one another, retraction of the needle results in the arms moving toward one another, away from the catheter hub's interior walls.

Embodiments of the disclosed devices may include additional and/or alternative structures. As shown in FIGS. 13-17, for example, a cannula 300 can include a safety clip 302 in addition to or instead of the aforementioned ball release mechanism to prevent accidental needle pricks. The cannula 300 can include a needle guard assembly 304 having a body portion 306 connected to a catheter hub 308 such that a projection 310 on the body portion 306 engages with a recess 311 in the catheter hub 308. The body portion 306 of the needle guard assembly 304 defines an inner bore 312 configured for receiving the safety clip 302. The safety clip 302 can be positioned within the body portion 306 such that the safety clip 302 engages with at least one interlocking flange 314 defined in the body portion 306. In its resting, biased configuration, the safety clip 302 can allow a needle to extend through the body portion 306 and the catheter hub 308. Upon withdrawal of the needle from the proximal end of the catheter hub 308, the safety clip 302 can disengage from the interlocking flange 314 and enclose a tip portion 316 of the needle 318 within the catheter hub 308, thereby preventing needle prick injuries during withdrawal of the needle 318 from a patient.

The body portion 306 can also feature a tubular sleeve 320 that extends axially from the catheter hub 308 up to a needle hub 322, connected to the body portion 306. The needle hub 322 is fixedly connected to the needle 318 and is in a tight-fit relationship with the body portion 306. As such, when the needle 318 is withdrawn from the needle hub 322, the needle hub 322 disengages from the body portion 306 and is withdrawn from the catheter hub 308, the needle hub 322 disengages from the body portion 306. Also, due to the construction of the safety clip 302 within the body portion 306, the safety clip 302 also disengages from the body portion 306 and is withdrawn along with the needle 318. As such, the tip portion 316 of the needle 318 is not exposed to the user during withdrawal of the needle 318 from a patient user. In some embodiments, the needle hub 322 may be provided with a thumb grip 324 for enabling a user to grip the cannula 300 during use.

The needle hub 322 can also be releasably coupled to a flow control hub 326 via an extended portion of the needle hub 322. A proximal end of the needle hub 322 can be closed using a threaded cap or a luer lock. The flow control hub 326 may include a flashback chamber 328, which may include a porous filter 330 and a cover to allow air to escape and blood to flow inside the flashback chamber 328. The flashback chamber 328 may additionally include a hydrophobic filter for preventing spillage of the blood therefrom.

As further shown, a catheter tube 332 can be fixedly connected to the distal end 333 of the catheter hub 308. The catheter tube 332 comprises a thin elongated tubular structure having a first chamber 334. The bore of the catheter tube 332 can be configured to encase the needle 318. The catheter hub 308 can also include an annular stopper 336 on an inner surface of the catheter hub 308. The annular stopper 336 is disposed at the proximal end of the catheter hub 308. In an embodiment, the luer lock cap is provided to seal the proximal end of the catheter hub 308. The catheter hub 308 is adapted to accommodate a tubular valve member 338 within the coaxial recess 340 of the hub, abutting a valve closure member 339. The tubular valve member 338 can define a flat distal surface. The tubular valve member 338 is configured to be held in place within the coaxial recess 340 of the catheter hub 308 when a first end of the tubular valve member 338 abuts the annular stopper 336.

Figure 15:
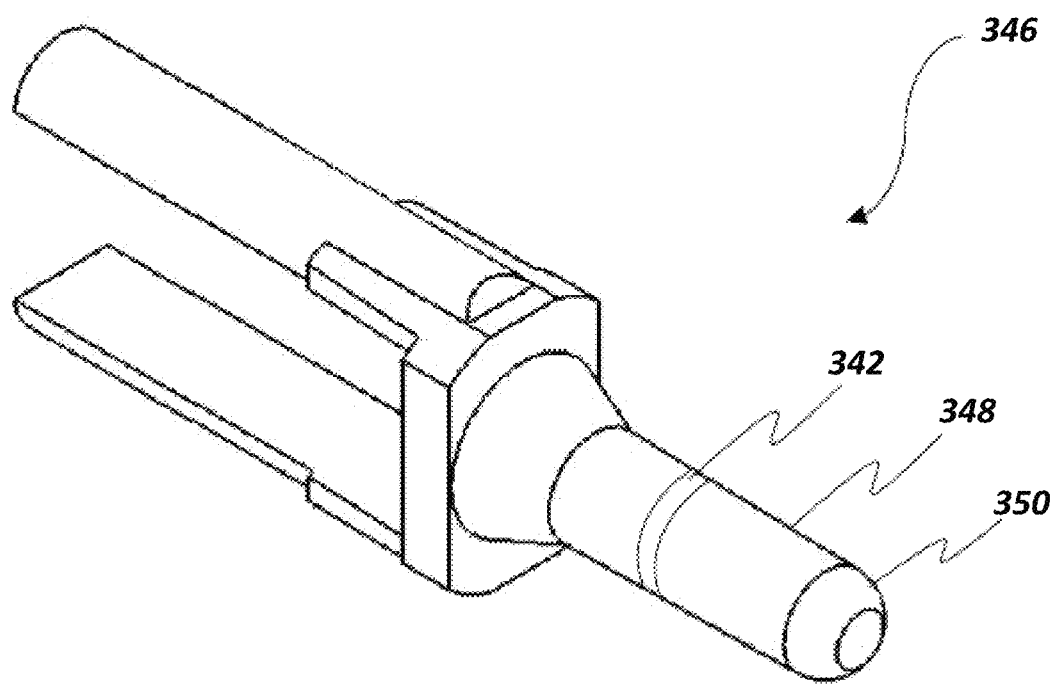
FIG. 15 is a perspective view of an actuator member of the cannula device shown in FIG. 13 according to embodiments of the present disclosure.
Figure 17:
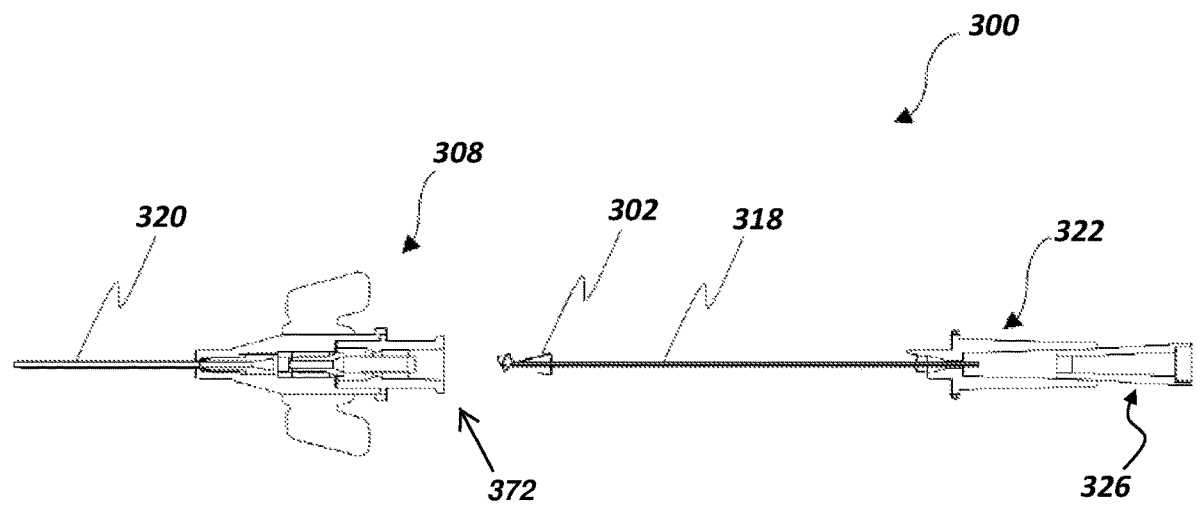
FIG. 17 is a cross-sectional view of the cannula device shown in FIG. 13 when the needle member is withdrawn from the catheter hub, according to embodiments of the present disclosure.

FIG. 15 is a perspective view of the actuator member 346 positioned within the cannula 300 in accordance with some embodiments of the present disclosure. The actuator member 346 includes a first end having a radially extending flange 348, a second end having a convex surface 350 and an axial bore between the first end and the second end. The actuator member 346 can also define a circular recess 342 on an outer surface, such that a protrusion of the tubular valve member 338 (e.g., protrusion 131) is configured to engage with the circular recess 342. The engagement of the protrusion and the circular recess 342 of the actuator member 346 ensures that the tubular valve member 338 and the actuator member 346 remain coupled and secure within the catheter hub 308.

FIG. 16 is a magnified perspective of the safety clip 302. The safety clip 302 is configured to block entry of the needle 318 into the catheter hub 308 and retain the tip portion 316 of the needle 318 therein, when the needle 318 is withdrawn from the catheter hub 308. The safety clip 302 includes a bracket 352 defining an opening 354 for receiving the needle 318. The opening 354 may be sized based on the diameter of the needle 318 to be employed in the cannula 300. The opening 354 allows the needle to move proximally through the safety clip 302 until the opening 354 reaches a bump, flattened portion, or protrusion near the distal end of the needle 318 that is larger than the opening 354, so that the safety clip 302 cannot slide off the distal end of needle 318. For example, the needle 318 can define a crimp 355 near its tip portion 316. The crimp 355 in the needle 318 can include a pair of generally opposed, outwardly extending bulges 355a and a pair of generally opposed, inwardly extending depressions 355b, which are disposed generally orthogonally with respect to the bulges 355a. The bulges 355a define the crimp 355 having a width, W, which is small enough to facilitate movement of the needle 318 within the cannula 300, but large enough to prevent passage of the distal end of the needle 318 through the opening 354.

A first resilient arm 356 extends from one end of the bracket 352 and has a first section 358 and a second section 360, and the dimensions of the first section 358 may be larger than the dimensions of the second section 360 in some embodiments. As an example, the first section 358 may be wider that the second section 360. Such a construction of the safety clip 302 renders effortless and inexpensive manufacturing of the safety clip 302, while ensuring sufficient spring force or biasing spring force requirements. The first section 358 may further conform to the dimensions of the bracket 352 and thus ensure uniformity in construction, which retains the structural rigidity of the safety clip 302 when subjected to deformation.

A second resilient arm 362 extends from another end of the bracket 352 and has a first section 364 and a second section 366, and the dimensions of the first section 364 may be larger than the second section 366 in some embodiments. As an example, the first section 364 may be wider than the second section 366. Such a construction of the safety clip 302 renders effortless and inexpensive manufacturing of the safety clip 302, while ensuring sufficient spring force or biasing force requirements. The first section 364 may further conform to the dimensions of the bracket 352 and thus ensure uniformity in construction, which retains the structural rigidity of the safety clip 302 when subjected to deformation.

A connection portion 368 is also included, preferably at the second section 360. The connection portion 368 is configured to engage with at least one interlocking flange 314 configured on an inner surface of the body portion 306 and the needle 318. The connection portion 368 is configured to engage with the interlocking flange 314 and a body 370 of the needle 318 for puncturing the vein of the subject. The connection portion 368 further disengages from the interlocking flange 314 and the body 370 of the needle 318 when the needle 318 is withdrawn from the proximal end 372 of the catheter hub 308.

The connection portion 368 includes a curved protrusion 374 at a fore end and a curved lip 376 at an aft end. The curved protrusion 374 is configured to engage with the interlocking flange 314 of the body portion 306, so that the safety clip 302 is held within the body portion 306. The curved lip 376 provided at the aft end extends inwardly toward the bracket 352 and is configured to engage the needle 318.

The curved protrusion 374 engages with the interlocking flange 314 due to biasing of the first and second resilient arms 356, 362. The first and second resilient arms 356, 362 are biased or flexed due to insertion of the needle 318 into the catheter hub 308. Insertion or presence of the needle 318 into the needle guard assembly 304 urges the first and second resilient arms 356, 362 to flex away from each other, thereby engaging the curved protrusion 374 to engage with the interlocking flange 314. At the same time, the curved lip 376 engages with the body 370 of the needle 318, so that the biasing force is maintained and the safety clip 302 is retained within the body portion 306.

In some embodiments, the curved protrusion 374 of the first and second arms 356, 362 are outwardly extending protrusions configured for engaging the interlocking flange 314 in the body portion 306, which are inwardly protruding. Accordingly, the construction or shape or configuration of the curved protrusion 374 may be selected based on the construction of the interlocking flanges 314, so that interlocking therebetween is ensured when the needle 318 is present in the catheter hub 308.

In another embodiment, the curved lip 376 of the first and second arms 356, 362 may comprise inwardly extending protrusions configured for engaging with the needle 318 when the needle 318 is present within the catheter hub 308, and enclose the tip portion 316 of the needle 318 within the safety clip 302 when the needle 318 is withdrawn from the catheter hub 308. As such, the curved lip 376 is configured to prevent entry or re-entry of the needle 318 beyond the safety clip 302, when the needle 318 is withdrawn from the catheter hub 308. Accordingly, the construction or shape or configuration of the curved lip 376 may be selected based on the configuration of the needle 318 or the position at which the needle is inserted or withdrawn. As one non-limiting example, the curved protrusion 374 may be an inverted U-shaped member, while the curved lip 376 may be a U-shaped member.

Further, the curved protrusion 374 on each of the first and the second arms 356, 362, can include a projection 378 extending toward the bracket 352. The projection 378 along with the second section of the respective arms defines a seat portion 380. The seat portion 380 is adapted to receive and seat the tip portion 316 of the needle 318, which may ensure that the tip portion 316 of the needle 318 rests within the safety clip 302, thereby preventing misalignment of the needle 318 during withdrawal from the catheter hub 308 or during disposal of the needle 318.

In an embodiment, the first resilient arm 356 is longer than the second resilient arm 362. Such a construction of the arms 356, 362 may be provided to ensure that sufficient biasing force is exerted onto the interlocking flanges 314 during use, thereby ensuring that the safety clip 302 is sufficiently retained within the body portion 306. Also, asymmetric lengths of the arms may ensure contact of the connection portion 368 on the body 370 of the needle 318 about the same plane. Such an engagement may ensure uniform stress-distribution on the needle 318, thereby preventing damage during assembly. In an embodiment, the needle 318 may be assembled into the catheter hub 308 in the body portion 306 by initially flexing the arms 356, 362 and thereafter inserting the needle 318 through the tubular sleeve 320.

Further, each of the bracket 352 and the first and the second resilient arms 356, 362 may be defined with at least one rib member 382. The rib member 382 reinforces the safety clip 302, which improves its overall strength. As an example, the rib member 382 may extend about the surface of the bracket 352. The rib member 382 may also extend along the second sections of the first and the second arms 356, 362, which inherently improves the strength of the second sections. The length of extension of the rib member 382 may be configured based on the strength or rigidity requirements of the safety clip 302. In an embodiment, the rib member 382 may be formed on the bracket 352 and/or the arms via conventional manufacturing techniques such as punching and the like.

In an embodiment, the rib member 382 may be provided on the bracket 352 as a reinforcement, in order to prevent damage to the bracket 352 via contact of a protuberance on the needle 318 during removal of the needle 318. Such a construction ensures that the needle 318 is retained within the safety clip 302 upon withdrawal. In some embodiments, the rib member 382 may be made of a metallic material, a plastic material, a composite material, or any other material which serves the purpose of providing reinforcement to the safety clip 302.

In an embodiment, the bracket 352 and the first and the second arms 356, 362 may be made of metallic material or any other material which serves the purpose of ensuring interlocking with the body portion 306 when the needle 318 is present within the catheter hub 308, and encloses the tip portion 316 within when the needle 318 is withdrawn from the catheter hub 308.

When the needle 318 is withdrawn after puncturing the vein, the slits of the tubular valve member will close since the tubular valve member is made of flexible material which can self-close the opening at the slits of the flat portion of the valve member. Additionally, once the tip portion 316 of the needle 318 is withdrawn from the proximal end 372, particularly, beyond the connection portion 368 of the arms 356, 362 of the safety clip 302, the biasing force acting on the arms 356, 362 due to contact with the needle 318 ceases. As such, the arms retract to an unbiased configuration, during which the curved lip 376 completely closes the path for the tip portion 316 to move forward and beyond the safety clip 302. Thus, the safety clip 302 retains the needle 318 upon withdrawal from the catheter hub 308. In this scenario, the safety clip 302 may be withdrawn from the body portion 306 along with the needle 318 via the needle hub 322.

The tip portion 316 rests on the seat portion 380 configured on the safety clip 302, and thus the alignment of the needle 318 is maintained, irrespective of movement of the needle 318 during withdrawal. Therefore, exposure of the tip portion 316 of the needle 318 is prevented and the likelihood of needle prick injuries reduced. In embodiments, the tip portion 316 may selectively rest on any of the seat portion 380 configured on the first and second arms 356, 362.

The disclosed intravenous cannula devices can prevent a patient's blood from contacting a user's hand(s) because the reverse, proximal flow of blood is blocked upon closure of the disclosed prongs of the tubular valve member. Blood-based infections and physical injuries may therefore be prevented as a result.

The disclosed intravenous cannula devices may be less expensive than alternative devices because the tubular valve member, the actuator member, and the valve closure member can be made of inexpensive plastic or bio-compatible material.

The disclosed intravenous cannula devices can provide improved closing of the slits defined by the tubular valve member because the plurality of prongs of the tubular valve member can be closed quickly and reliably via the pushing force acting towards the proximal end of the catheter hub by the valve closure member, thereby closing the internal fluid passage defined by the device without allowing reverse flow of blood.

The disclosed cannula devices may prevent the tip of the needle from contacting a user after withdrawing the needle. For instance, the disclosed needle safety components provide a safety mechanism in the form of one or more safety release components that shield the tip of the needle when the needle is withdraw after piercing a blood vessel of a patient.

The disclosed locking elements, which can include solid spherical balls in some examples, provide selective disengagement of a catheter assembly from a needle guard assembly upon proximal retraction of the needle into the needle guard assembly, thereby preventing exposure of needle tip and needle prick injuries commonly associated therewith.

The disclosed locking elements comprising solid spherical balls enable the easy removal of the needle by unlocking the locking engagement of the catheter assembly and needle guard assembly.

Figure 18:
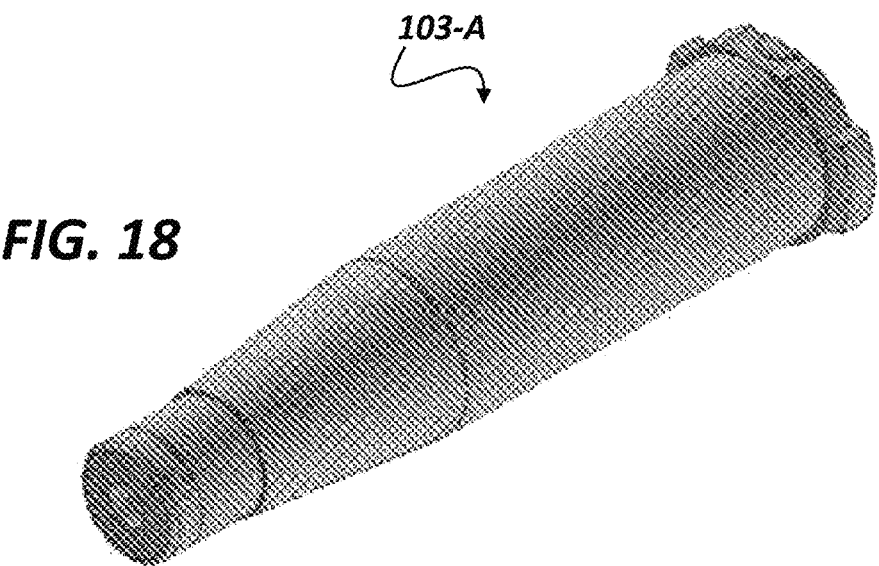
FIG. 18 is a perspective view of an example of a catheter hub in accordance with embodiments of the present disclosure.
Figure 19:
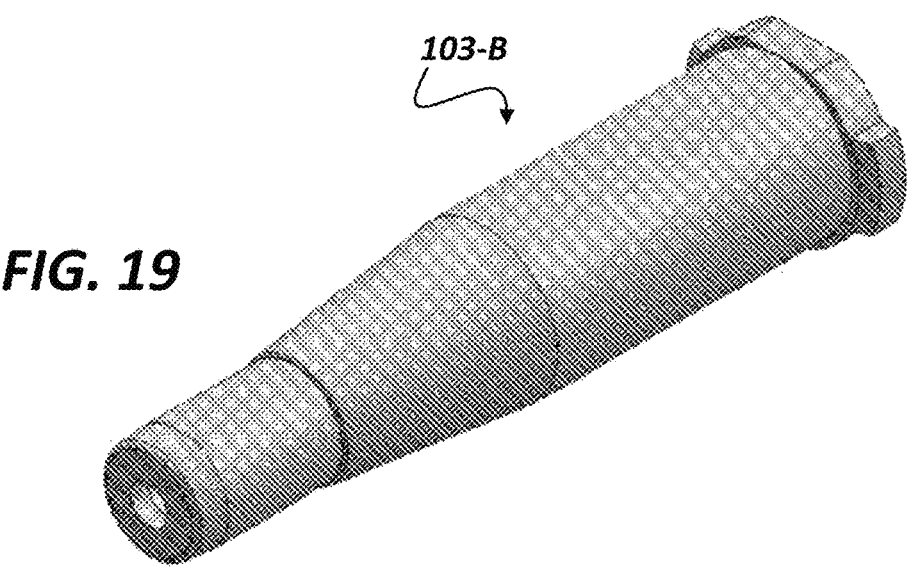
FIG. 19 is a perspective view of another example of a catheter hub in accordance with embodiments of the present disclosure.
Figure 20:
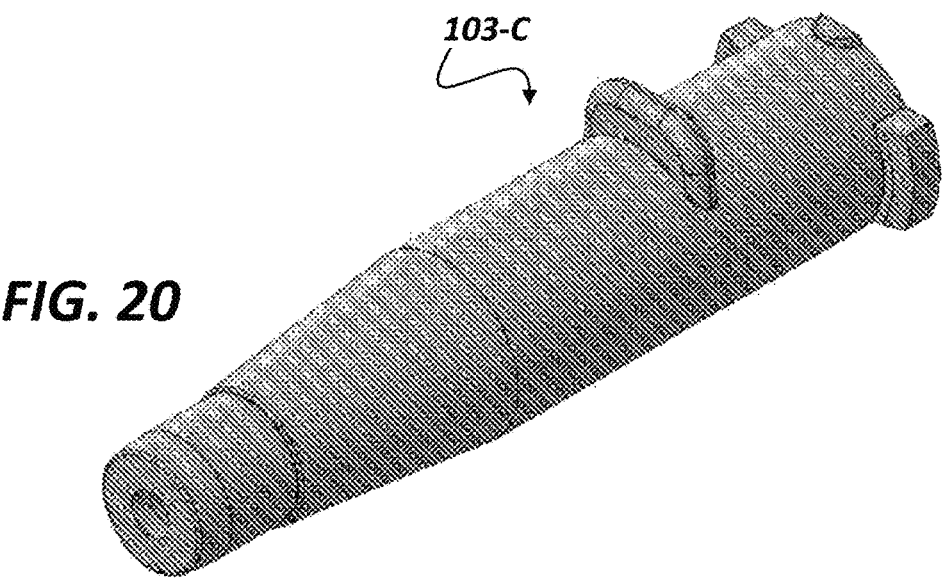
FIG. 20 is a perspective view of another example of a catheter hub in accordance with embodiments of the present disclosure.

The disclosed devices can include or be compatible with various types of catheter hubs, including but not limited to hubs 103-A, 103-B, and 103-C shown in FIG. 18, FIG. 19 and FIG. 20, respectively. The disclosed tubular valve members, actuator members, and valve closure members, among other components, may therefore not be limited to cannulas having the catheter hubs represented in FIGS. 1 and 13.

Embodiments described herein may also be configured to have additional or alternative needle release and retraction mechanisms. For example, embodiments of the disclosed cannulas can include a coiled spring biased to retract the needle proximally, such that the needle is automatically retracted and enclosed within the needle guard assembly after and before its deployment. Embodiments may also feature a push-button mechanism configured to facilitate release and retraction of the needle, and/or to facilitate coupling and uncoupling of the catheter assembly with the needle guard assembly. Embodiments may include a manually operable push-button protruding from, or accessible at, a surface of a cannula, extending outwardly from the needle guard assembly in some examples. Actuation of the push-button may be necessary to overcome a spring force biasing the needle in the proximal direction, within the needle guard assembly. Outward displacement of the push-button may allow the internal components of the needle guard assembly, e.g., the needle hub, to move distally in unison with the needle attached thereto. Examples of spring-biased, push-button activated cannula configurations compatible with one or more of the disclosed embodiments are described in U.S. Pat. No. 4,747,831, the entire contents of which are incorporated by reference herein.

While aspects of the present invention have been particularly shown and described with reference to the embodiments above, it will be understood by those skilled in the art that various additional embodiments may be contemplated by modification of the disclosed device without departing from the scope of what is disclosed. Such embodiments should be understood to fall within the scope of the present invention as determined based upon claims and any equivalents thereof.

The invention claimed is:

1. An intravenous cannula device comprising:
 a catheter hub having a proximal end, a distal end, and a coaxial recess extending from the proximal end to the distal end;
 a tubular valve member disposed within the coaxial recess of the catheter hub, the tubular valve member comprising:
  a cylindrical portion defining a longitudinal recess; and
  a distal surface comprising one or more slits that define a plurality of prongs, the one or more slits are configured to open and close upon movement of a needle therethrough;
 an actuator member having an axial bore, the actuator member disposed within the longitudinal recess of the tubular valve member, wherein distal displacement of the actuator member within the catheter hub opens the plurality of prongs of the tubular valve member and forms a passage for a fluid flow from the proximal end of the catheter hub to the distal end of the catheter hub;
 a valve closure member comprising a proximal end, a distal end, and a through-hole extending from the proximal end of the valve closure member to the distal end of the valve closure member, the valve closure member being disposed within the catheter hub such that the proximal end of the valve closure member abuts an undercut portion of the catheter hub and the distal end of the valve closure member abuts a distal end of the tubular valve member;
 a needle guard assembly configured to push the needle distally, withdraw the needle proximally, enclose the needle therein, and reversibly couple with the proximal end of the catheter hub; and
 a safety release component fixed to a distal end of the needle guard assembly, the safety release component comprising a body having a longitudinal bore extending therethrough, at least one groove defined by an outer surface of the body, and one or more moveable locking elements each configured to engage with an annular groove defined by a proximal cylindrical portion of the catheter hub,
 wherein the one or more moveable locking elements are spherical and complementary to the at least one groove defined by the outer surface of the body of the safety release component, and
 wherein the one or more moveable locking elements are configured to be displaced away from the at least one groove and the longitudinal bore upon insertion of the needle through the longitudinal bore such that the one or more moveable locking elements each engage with the annular groove and lock the needle guard assembly to the catheter hub.

2. The intravenous cannula device of claim 1, wherein the valve closure member has hardness ranging from about 50 Shore to about 80 Shore, and the tubular valve member has hardness ranging from about 20 Shore to about 45 Shore.

3. The intravenous cannula device of claim 1, wherein the tubular valve member is configured to be held in place within the coaxial recess of the catheter hub when a first end of the tubular valve member abuts an annular stopper of the catheter hub.

4. The intravenous cannula device of claim 1, wherein the tubular valve member is made of a flexible material comprising silicone, rubber, or both.

5. The intravenous cannula device of claim 1, wherein the one or more slits form a Y-shape, an inverted Y-shape, an X-shape, a + shape, or a combination thereof.

6. The intravenous cannula device of claim 1, wherein the cylindrical portion of the tubular valve member comprises a radially extending protrusion at an inner surface thereof.

7. The intravenous cannula device of claim 6, wherein the actuator member comprises a circular recess at an outer surface configured to engage with the radially extending protrusion of the tubular valve member.

8. The intravenous cannula device as claimed in claim 1, wherein the actuator member comprises a radially extending flange.

9. The intravenous cannula device of claim 1, wherein the actuator member comprises a rigid plastic material or metal.

10. The intravenous cannula device of claim 1, further comprising a flashback chamber comprising a porous filter and/or a cover configured to allow air to escape therefrom and blood to flow therein.

11. The intravenous cannula device of claim 1, wherein the one or more moveable locking elements are configured to settle within the at least one groove after withdrawal of the needle from the longitudinal bore.

12. The intravenous cannula device of claim 1, wherein the distal surface of the tubular valve member is substantially flat.

13. The intravenous cannula device of claim 1, wherein the distal surface of the tubular valve member is convex.

14. The intravenous cannula device of claim 1, further comprising a luer lock member coupled to the needle guard assembly.

15. The intravenous cannula device of claim 1, wherein the valve closure member is configured to close the plurality of prongs of the tubular valve member, thereby preventing blood flow from the distal end of the catheter hub to the proximal end of the catheter hub.

16. The intravenous cannula device of claim 1, further comprising a catheter tube extending distally from the distal end of the catheter hub, the catheter tube defining an inner lumen sized to accommodate passage of the needle therethrough.

17. An intravenous cannula device comprising:
a catheter assembly comprising a catheter hub having a distal end connected to a proximal end of a catheter tube, wherein an inner surface of a proximal portion of the catheter hub comprises an annular groove;
a needle guard assembly configured to couple with a proximal end of the catheter assembly, the needle guard assembly comprising:
an elongated tubular member;
a needle hub comprising a needle holder disposed within the elongated tubular member, wherein a distal end of the needle holder is connected with a needle; and
a safety release component fixed to a distal end of the elongated tubular member, wherein the safety release component comprises a body and one or more moveable locking elements configured to releasably couple with the catheter hub, each of the one or more moveable locking elements is sized to fit within one of one or more complementary grooves defined by an outer surface of the body; and
wherein each of the one or more moveable locking elements is configured to engage with the annular groove of the catheter hub by moving radially outward from one of the one or more complementary grooves, thereby coupling the elongated tubular member of the needle guard assembly with the catheter assembly when the needle is passed through the safety release component pursuant to puncturing a blood vessel of a patient.

18. The intravenous cannula device of claim 17, wherein the body of the safety release component further comprises an axial bore through which the needle is passed.

19. The intravenous cannula device of claim 17, wherein the one or more moveable locking elements are spherical.

20. The intravenous cannula device of claim 19, wherein the one or more moveable locking elements are made of stainless steel.

21. The intravenous cannula device of claim 17, wherein the safety release component comprises a circular base portion fixed to the distal end of the elongated tubular member.

22. The intravenous cannula device of claim 21, wherein the safety release component comprises a tubular portion extending from the circular base portion and defining an axial bore configured to accommodate passage of the needle therethrough.

23. The intravenous cannula device of claim 22, wherein each of the one or more complementary grooves extends toward the axial bore of the tubular portion of the safety release component.

24. The intravenous cannula device of claim 23, wherein each of the one or more moveable locking elements is configured to settle within one of the one or more complementary grooves after withdrawal of the needle from the axial bore.

25. An intravenous cannula device comprising:
a catheter hub having a proximal end, a distal end, and a coaxial recess extending from the proximal end to the distal end;
a tubular valve member disposed within the coaxial recess of the catheter hub, the tubular valve member comprising:
a cylindrical portion defining a longitudinal recess; and
a distal surface comprising one or more slits that define a plurality of prongs, the one or more slits configured to open and close upon movement of a needle therethrough;
an actuator member having an axial bore, the actuator member disposed within the longitudinal recess of the tubular valve member, wherein distal displacement of the actuator member within the catheter hub opens the plurality of prongs of the tubular valve member and forms a passage for a fluid flow from the proximal end of the catheter hub to the distal end of the catheter hub;

a valve closure member comprising a proximal end, a distal end, and a through-hole extending from the proximal end of the valve closure member to the distal end of the valve closure member, the valve closure member being disposed within the catheter hub such that the proximal end of the valve closure member abuts an undercut portion of the catheter hub and the distal end of the valve closure member abuts a distal end of the tubular valve member; and a needle guard assembly configured to couple with the proximal end of the catheter hub, the needle guard assembly comprising:

an elongated tubular member;

a needle hub comprising a needle holder disposed within the elongated tubular member, wherein a distal end of the needle holder is connected with the needle; and a safety release component fixed to a distal end of the elongated tubular member, wherein the safety release component comprises a body, at least one groove defined by an outer surface thereof, and one or more moveable locking elements complementary to the at least one groove and configured to releasably couple with the catheter hub, wherein the one or more moveable locking elements are configured to be displaced away from the at least one groove and engage with the proximal end of the catheter hub, thereby coupling the elongated tubular member of the needle guard assembly with the catheter hub when the needle is passed through the safety release component pursuant to puncturing a blood vessel of a patient.

26. The intravenous cannula device of claim 1, wherein a diameter of the at least one groove is slightly greater than or substantially equal to a diameter of each of the one or more moveable locking elements.

\* \* \* \* \*